United States Patent
Lopez

(10) Patent No.: US 11,274,160 B2
(45) Date of Patent: Mar. 15, 2022

(54) ANTIBODIES HAVING SPECIFICITY TO NECTIN-4 AND USES THEREOF

(71) Applicants: INSERM (INSTITUT NATIONAL DE LA SANTE ET DE LA RECHERCHE MEDICALE), Paris (FR); INSTITUT JEAN PAOLI & IRENE CALMETTES, Marseilles (FR); CENTRE NATIONAL DE LA RECHERCHE SCIENTIFIQUE (CNRS), Paris (FR); UNIVERSITE D'AIX MARSEILLE, Marseilles (FR)

(72) Inventor: Marc Lopez, Marseill (FR)

(73) Assignees: INSERM (Institut National de la Santé et de la Recherche Médicale, Paris (FR); INSTITUT JEAN PAOLI & IRENE CALETTES, Marseilles (FR); CENTRE NATIONALE DE LA RECHERCHE SCIENTIFIQUE, Paris (FR); UNIVERSITE D'AIX MARSEILLE, Marseilles (FR)

( * ) Notice: Subject to any disclaimer, the term of this patent is extended or adjusted under 35 U.S.C. 154(b) by 264 days.

(21) Appl. No.: 16/490,388

(22) PCT Filed: Mar. 1, 2018

(86) PCT No.: PCT/EP2018/055109
§ 371 (c)(1),
(2) Date: Aug. 30, 2019

(87) PCT Pub. No.: WO2018/158398
PCT Pub. Date: Sep. 7, 2018

(65) Prior Publication Data
US 2021/0324104 A1 Oct. 21, 2021

(30) Foreign Application Priority Data
Mar. 2, 2017 (EP) .................................. 17305226

(51) Int. Cl.
*C07K 16/30* (2006.01)
*A61P 35/00* (2006.01)
*A61K 47/68* (2017.01)
*A61K 45/06* (2006.01)
*A61K 39/00* (2006.01)

(52) U.S. Cl.
CPC ............. *C07K 16/30* (2013.01); *A61K 45/06* (2013.01); *A61K 47/6803* (2017.08); *A61K 47/6851* (2017.08); *A61K 2039/505* (2013.01); *C07K 2317/24* (2013.01); *C07K 2317/565* (2013.01)

(58) Field of Classification Search
CPC ................ C07K 16/30; C07K 2317/24; C07K 2317/565; A61K 47/6803; A61K 47/6851; A61K 2039/505; A61P 35/00
USPC ....................................... 424/134.1
See application file for complete search history.

(56) References Cited

FOREIGN PATENT DOCUMENTS

WO 2017/042210 A1 3/2017

OTHER PUBLICATIONS

Anonymous: "A study of the Safety and Pharmacokinetics of AGS-22M6E in Subjects With Malignant Solid Tumors That Express Nectin-4", Internet Citation, Jun. 22, 2015.
Anonymous: "A Study of Escalating Doses of ASG-22CE Given as Monotherapy in Subjects With Metastatic Urothelial Cancer and Other Malignant Solid Tumors That Express Nectin-4", retrieved from the internet, Mar. 18, 2014.
Chalita-Eid et al: "Enfortumab Vedotin Antibody-Drug Conjugate Targeting Nectin-4 Is a Highly Potent Therapeutic Agent in Multiple Preclinical Cancer Models", Cancer Research, vol. 76, No. 10, pp. 3003-3013, May 15, 2016.
Pavlova et al: "A role for PVRL4-driven cell-cell interactions in tumorgenesis", ELIFE, vol. 2, Apr. 30, 2013.
Petrylak et al: "A phase I study of enfortumab vedotin (ASG-22CE; ASG-22ME): Updated analysis of patients with metastatic urothelial cancer : 2017 ASCO Annual Meeting Abstracts", J Clin Oncol, Jun. 5, 2017.

*Primary Examiner* — Yan Xiao
(74) *Attorney, Agent, or Firm* — WC&F IP

(57) ABSTRACT

The present invention relates to a new antibody anti-nectin-4. Nectin-4 is a tumor-associated antigen overexpressed in several cancers and notably in 30%, 49% and 86% of breast, ovarian and lung carcinomas, respectively, which are tumors of bad prognosis. Treatments remain still elusive. That's why the inventors developed a new targeted therapy based on an antibody having specificity to nectin-4 (called 14A5.2 mab). Indeed, the inventors selected this antibody for its intrinsic prophylactic anti-metastatic properties and also for the treatment of localized primary and metastatic cancer. More, the 14A5.2 mab could be indicated for the treatment of cancer resistant to ASG-22ME (from Astellas company). Thus, the invention relates to the 14A5.2 mab and its uses thereof.

Figure 1:
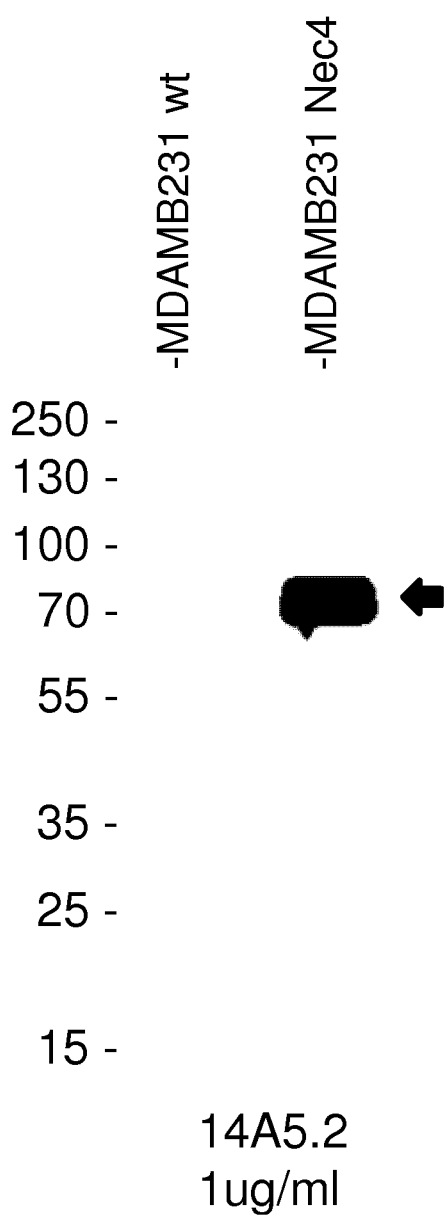

10 Claims, 7 Drawing Sheets
Specification includes a Sequence Listing.

ANTIBODIES HAVING SPECIFICITY TO NECTIN-4 AND USES THEREOF

FIELD OF THE INVENTION

The present invention relates to antibody having specificity to nectin-4 and uses thereof.

BACKGROUND OF THE INVENTION

Nectin-4 is a surface molecule that belongs to the nectin family of proteins, which comprises 4 members. Nectins are cell adhesion molecules that play a key role in various biological processes such as polarity, proliferation, differentiation and migration, for epithelial, endothelial, immune and neuronal cells, during development and adult life. They are involved in several pathological processes in humans. They are the main receptors for poliovirus, herpes simplex virus and measles virus. Mutations in the genes encoding Nectin-1 (PVRL1) or Nectin-4 (PVRL4) cause ectodermal dysplasia syndromes associated with other abnormalities. Nectin-4 is expressed during fetal development. In adult tissues its expression is more restricted than that of other members of the family. Nectin-4 is a tumor-associated antigen in 30%, 49% and 86% of breast, ovarian and lung carcinomas, respectively, mostly on tumors of bad prognosis. Its expression is not detected in the corresponding normal tissues. In breast tumors, Nectin-4 is expressed mainly in triple-negative carcinomas. In the serum of patients with these cancers, the detection of soluble forms of Nectin-4 is associated with a poor prognosis. Levels of serum Nectin-4 increase during metastatic progression and decrease after treatment. These results suggest that Nectin-4 could a reliable target for the treatment of cancer. Accordingly, several anti-Nectin-4 antibodies have been described in the prior art. In particular, Enfortumab Vedotin (ASG-22ME) is an antibody-drug conjugate (ADC) targeting Nectin-4 and is currently clinically investigated for the treatment of patients suffering from solid tumors.

SUMMARY OF THE INVENTION

The present invention relates to antibody having specificity to nectin-4 and uses thereof. In particular, the present invention is defined by the claims.

DETAILED DESCRIPTION OF THE INVENTION

The present invention relates to antibody (particularly a monoclonal antibody) having specificity to Nectin-4 and uses thereof. In particular, the present invention provides antibody that derives from the 14A5.2 antibody (also called 14A5.2 mab). Indeed, the inventors selected this antibody for its intrinsic anti-metastatic properties. Also, they showed that the 14A5.2 recognizes, with a similar affinity, an epitope different from the epitope recognizes by the Ha22-2 antibody (also known as ASG-22ME from Astellas company). The 14A5.2 could be indicated for preventing the metastatic disease and/or for the treatment of localized primary or metastatic cancer. More, the 14A5.2 could be indicated for the treatment of cancer resistant to ASG-22ME.

As used herein, the term "Nectin-4 has its general meaning in the art and includes human Nectin-4, in particular the native-sequence polypeptide, isoforms, chimeric polypeptides, all homologs, fragments, and precursors of human Nectin-4. The amino acid sequence for native Nectin-4 includes the NCBI Reference Sequence: NP_112178.2.

According to the present invention, the VH region of the 14A5.2 mab consists of the sequence of SEQ ID NO: 1. Accordingly, the H-CDR1 of 14A5.2 mab is defined by the sequence ranging from the amino acid residue at position 31 to the amino acid residue at position 35 in SEQ ID NO: 1. Accordingly, the H-CDR2 of 14A5.2 mab is defined by the sequence ranging from the amino acid residue at position 50 to the amino acid residue at position 66 in SEQ ID NO: 1. Accordingly, the H-CDR3 of 14A5.2 mab is defined by the sequence ranging from the amino acid residue at position 99 to the amino acid residue at position 104 in SEQ ID NO:1.

```
SEQ ID NO: 1: VH region of 14A5.2 mab FR1-CDR1-
FR2-CDR2-FR3-CDR3-FR4
EVLLQQSGPELVKPGASVKIPCKASGYTFTDYTMDWVKQSHGKSLEWIG
DINPNNDVTMYNEKFKGRATLTVDKSSTAYMEVRSLTSEDTAVYYCVR
GRGFAYWGQGTLVTVSA
```

According to the present invention, the VL region of the 14A5.2 mab antibody consists of the sequence of SEQ ID NO:2. Accordingly, the L-CDR1 of 14A5.2 mab is defined by the sequence ranging from the amino acid residue at position 24 to the amino acid residue at position 38 in SEQ ID NO:2. Accordingly, the L-CDR2 of 14A5.2 mab is defined by the sequence ranging from the amino acid residue at position 54 to the amino acid residue at position 60 in SEQ ID NO:2. Accordingly, the L-CDR3 of 14A5.2 mab is defined by the sequence ranging from the amino acid residue at position 93 to the amino acid residue at position 101 in SEQ ID NO:2.

```
SEQ ID NO: 2: VL region of 14A5.2 mab antibody
FR1-CDR1-FR2-CDR2-FR3-CDR3-FR4
DIVLTQSPASLIVSLGQRATISCRASQSVSTSSNSYMHWYQQKPGQPPK
LLIRFASNLESGVPARFSGSGSGTYFTLNIHPVEEEDSATYYCQHSWEI
PYTFGGGTKLEIK
```

As used herein the term "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDR set from each of a heavy and a light chain V region. Framework Regions (FRs) refer to amino acid sequences interposed between CDRs. In one embodiment, the antibody of the invention is a monoclonal antibody.

In the context of the invention, the amino acid residues of the antibody of the invention are numbered according to the IMGT numbering system. The IMGT unique numbering has been defined to compare the variable domains whatever the antigen receptor, the chain type, or the species (Lefranc M.-P., "Unique database numbering system for immunogenetic analysis" Immunology Today, 18, 509 (1997); Lefranc M.-P., "The IMGT unique numbering for Immunoglobulins, T cell receptors and Ig-like domains" The Immunologist, 7, 132-136 (1999).; Lefranc, M.-P., Pommié, C., Ruiz, M., Giudicelli, V., Foulquier, E., Truong, L., Thouvenin-Contet, V. and Lefranc, G., "IMGT unique numbering for immunoglobulin and T cell receptor variable domains and Ig superfamily V-like domains" Dev. Comp. Immunol., 27, 55-77 (2003).). In the IMGT unique numbering, the conserved amino acids always have the same position, for instance cysteine 23, tryptophan 41, hydrophobic amino acid 89, cysteine 104, phenylalanine or tryptophan 118. The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. If the CDR3-IMGT length is less than 13 amino acids, gaps are created from the top of the loop, in the following order 111, 112, 110, 113, 109, 114, etc. If the CDR3-IMGT length is more than 13 amino acids, additional positions are created between positions 111 and 112 at the top of the CDR3-IMGT loop in the following order 112.1, 111.1, 112.2, 111.2, 112.3, 111.3, etc. (http://www.imgt.org/IMGTScientificChart/Nomenclature/IMGT-FRCDRdefinition.html).

As used herein, the term "specificity" refers to the ability of an antibody to detectably bind an epitope presented on an antigen, such as Nectin-4, while having relatively little detectable reactivity with non-Nectin-4 proteins or structures (such as other proteins presented on cancerous cell, or on other cell types). Specificity can be relatively determined by binding or competitive binding assays, using, e.g., Biacore instruments, as described elsewhere herein. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules (in this case the specific antigen is Nectin-4).

The term "affinity", as used herein, means the strength of the binding of an antibody to an epitope. The affinity of an antibody is given by the dissociation constant Kd, defined as $[Ab] \times [Ag]/[Ab-Ag]$, where $[Ab-Ag]$ is the molar concentration of the antibody-antigen complex, $[Ab]$ is the molar concentration of the unbound antibody and $[Ag]$ is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope.

The antibodies of the present invention are produced by any technique known in the art, such as, without limitation, any chemical, biological, genetic or enzymatic technique, either alone or in combination. Typically, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In one embodiment, the monoclonal antibody of the invention is a chimeric antibody, particularly a chimeric mouse/human antibody.

According to the invention, the term "chimeric antibody" refers to an antibody which comprises a VH domain and a VL domain of a non-human antibody, and a CH domain and a CL domain of a human antibody.

In some embodiments, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art (See Morrison S L. et al. (1984) and patent documents U.S. Pat. Nos. 5,202,238; and 5,204,244).

In another embodiment, the monoclonal antibody of the invention is a humanized antibody. In particular, in said humanized antibody, the variable domain comprises human acceptor frameworks regions, and optionally human constant domain where present, and non-human donor CDRs, such as mouse CDRs.

In another embodiment, the monoclonal antibody of the invention is a caninized or primatized based on the same methods of humanization.

According to the invention, the term "humanized antibody" refers to an antibody having variable region framework and constant regions from a human antibody but retains the CDRs of a previous non-human antibody.

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell. The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Examples of tandem type humanized antibody expression vector include pKANTEX93 (WO 97/10354), pEE18 and the like. Methods for producing humanized antibodies based on conventional recombinant DNA and gene transfection techniques are well known in the art (See, e.g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

In one embodiment, the antibody of the invention is an antigen biding fragment selected from the group consisting of a Fab, a F(ab)'2, a single domain antibody, a ScFv, a Sc(Fv)2, a diabody, a triabody, a tetrabody, an unibody, a minibody, a maxibody, a small modular immunopharmaceutical (SMIP), minimal recognition units consisting of the amino acid residues that mimic the hypervariable region of an antibody as an isolated complementary determining region (CDR), and fragments which comprise or consist of the VL or VH chains as well as amino acid sequence having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of identity with SEQ ID NO:1 or SEQ ID NO:2.

In some embodiments, the antibody of the present invention is an antibody having a heavy chain comprising i) the H-CDR1 of 14A5.2 mab, ii) the H-CDR2 of 14A5.2 mab and iii) the H-CDR3 of 14A5.2 mab and a light chain comprising i) the L-CDR1 of 14A5.2 mab, ii) the L-CDR2 of 14A5.2 mab and iii) the L-CDR3 of 14A5.2 mab.

In some embodiments, the antibody of the present invention is an antibody having a heavy chain having at least 70% of identity with SEQ ID NO:1 and a light chain having at least 70% of identity with SEQ ID NO:2.

In some embodiments, the antibody of the present invention is an antibody having a heavy chain identical to SEQ ID NO:1 and a light chain identical to SEQ ID NO:2.

In another embodiment, the antibody of the present invention is an antibody comprising:

a heavy chain comprising i) a H-CDR1 having at least 90% of identity with the H-CDR1 of 14A5.2 mab, ii) a H-CDR2 having at least 90% of identity with the H-CDR2 of 14A5.2 mab and iii) a H-CDR3 having at least 90% of identity with the H-CDR3 of 14A5.2 mab and a light chain comprising i) a L-CDR1 having at least 90% of identity with the L-CDR1 of 14A5.2 mab, ii) a L-CDR2 having at least 90% of identity with the L-CDR2 of 14A5.2 mab and iii) a L-CDR3 having at least 90% of identity with the L-CDR3 of 14A5.2 mab Wherein the H-CDR1 of 14A5.2 mab is defined by the sequence ranging from the amino acid residue at position 31 to the amino acid residue at position 35 in SEQ ID NO:1;

the H-CDR2 of 14A5.2 mab is defined by the sequence ranging from the amino acid residue at position 50 to the amino acid residue at position 66 in SEQ ID NO:1;

the H-CDR3 of 14A5.2 mab is defined by the sequence ranging from the amino acid residue at position 99 to the amino acid residue at position 104 in SEQ ID NO:1;

the L-CDR1 of 14A5.2 mab is defined by the sequence ranging from the amino acid residue at position 24 to the amino acid residue at position 38 in SEQ ID NO:2;

the L-CDR2 of 14A5.2 mab is defined by the sequence ranging from the amino acid residue at position 54 to the amino acid residue at position 60 in SEQ ID NO:2 and the L-CDR3 of 14A5.2 mab is defined by the sequence ranging from the amino acid residue at position 93 to the amino acid residue at position 101 in SEQ ID NO:2.

The term "antigen binding fragment" of an antibody, as used herein, refers to one or more fragments of an intact antibody that retain the ability to specifically binds to a given antigen (e.g., [nectin-4]). Antigen biding functions of an antibody can be performed by fragments of an intact antibody. Examples of biding fragments encompassed within the term antigen biding fragment of an antibody include a Fab fragment, a monovalent fragment consisting of the VL, VH, CL and CH1 domains; a Fab' fragment, a monovalent fragment consisting of the VL, VH, CL, CH1 domains and hinge region; a F(ab')2 fragment, a bivalent fragment comprising two Fab' fragments linked by a disulfide bridge at the hinge region; an Fd fragment consisting of VH domains of a single arm of an antibody; a single domain antibody (sdAb) fragment (Ward et al., 1989 Nature 341:544-546), which consists of a VH domain or a VL domain; and an isolated complementary determining region (CDR). Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (ScFv); see, e.g., Bird et al., 1989 Science 242:423-426; and Huston et al., 1988 proc. Natl. Acad. Sci. 85:5879-5883). "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2. Such single chain antibodies include one or more antigen biding portions or fragments of an antibody. These antibody fragments are obtained using conventional techniques known to those skilled in the art, and the fragments are screened for utility in the same manner as are intact antibodies. A unibody is another type of antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies. Antigen binding fragments can be incorporated into single domain antibodies, SMIP, maxibodies, minibodies, intrabodies, diabodies, triabodies and tetrabodies (see, e.g., Hollinger and Hudson, 2005, Nature Biotechnology, 23, 9, 1126-1136). The term "diabodies" "tribodies" or "tetrabodies" refers to small antibody fragments with multivalent antigen-binding sites (2, 3 or four), which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Antigen biding fragments can be incorporated into single chain molecules comprising a pair of tandem Fv segments (VH-CH1-VH-CH1) Which, together with complementary light chain polypeptides, form a pair of antigen binding regions (Zapata et al., 1995 Protein Eng. 8(10); 1057-1062 and U.S. Pat. No. 5,641,870).

The Fab of the present invention can be obtained by treating an antibody which specifically reacts with [antigen] with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with [antigen] with a protease, pepsin. Also, the F(ab')2 can be produced by binding Fab' described below via a thioether bond or a disulfide bond.

The Fab' of the present invention can be obtained treating F(ab')2 which specifically reacts with [antigen] with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well-known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. Nos. 5,859,205; 5,585,089; U.S. Pat. No. 4,816,567; EP0173494).

Domain Antibodies (dAbs) are the smallest functional binding units of antibodies—molecular weight approximately 13 kDa—and correspond to the variable regions of either the heavy (VH) or light (VL) chains of antibodies. Further details on domain antibodies and methods of their production are found in U.S. Pat. Nos. 6,291,158; 6,582,915; 6,593,081; 6,172,197; and 6,696,245; US 2004/0110941; EP 1433846, 0368684 and 0616640; WO 2005/035572, 2004/101790, 2004/081026, 2004/058821, 2004/003019 and 2003/002609, each of which is herein incorporated by reference in its entirety.

UniBodies are another antibody fragment technology, based upon the removal of the hinge region of IgG4 antibodies. The deletion of the hinge region results in a molecule that is essentially half the size of a traditional IgG4 antibody and has a univalent binding region rather than a bivalent binding region. Furthermore, because UniBodies are about smaller, they may show better distribution over larger solid tumors with potentially advantageous efficacy. Further details on UniBodies may be obtained by reference to WO 2007/059782, which is incorporated by reference in its entirety.

Nucleic Acid Sequence, Vectors and Host Cells

Accordingly, a further object of the invention relates to a nucleic acid molecule encoding an antibody according to the invention. More particularly the nucleic acid molecule encodes a heavy chain or a light chain of an antibody of the present invention.

Typically, said nucleic acid is a DNA or RNA molecule, which may be included in any suitable vector, such as a plasmid, cosmid, episome, artificial chromosome, phage or a viral vector. As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. So, a further aspect of the invention relates to a vector comprising a nucleic acid of the invention. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like. Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further aspect of the invention relates to a host cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce an antibody of the present invention in a suitable expression system. The term "expression system" means a host cell and compatible vector under suitable conditions, e.g. for the expression of a protein coded for by foreign DNA carried by the vector and introduced to the host cell. Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention.

Antibodies of the present invention are suitably separated from the culture medium by conventional immunoglobulin purification procedures such as, for example, protein A-Sepharose, hydroxylapatite chromatography, gel electrophoresis, dialysis, or affinity chromatography.

Functional Variants

The present invention thus provides antibodies comprising functional variants of the VL region, VH region of 14A5.2 mab. A functional variant of a VL or VH used in the context of a monoclonal antibody of the present invention still allows the antibody to retain at least a substantial proportion (at least about 50%, 60%, 70%, 80%, 90%, 95% or more) of the affinity/avidity and/or the specificity/selectivity of the parent antibody (i.e. 14A5.2 mab) and in some cases such a monoclonal antibody of the present invention may be associated with greater affinity, selectivity and/or specificity than the parent Ab. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation. Such functional variants typically retain significant sequence identity to the parent Ab. The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, (e.g., about 65-95%, such as about 92%, 93% or 94%) of the substitutions in the variant are conservative amino acid residue replacements. The sequences of CDR variants may differ from the sequence of the CDRs of the parent antibody sequences through mostly conservative substitutions; for instance at least 10, such as at least 9, 8, 7, 6, 5, 4, 3, 2 or 1 of the substitutions in the variant are conservative amino acid residue replacements. In the context of the present invention, conservative substitutions may be defined by substitutions within the classes of amino acids reflected as follows:

Aliphatic residues I, L, V, and M
Cycloalkenyl-associated residues F, H, W, and Y
Hydrophobic residues A, C, F, G, H, I, L, M, R, T, V, W, and Y
Negatively charged residues D and E
Polar residues C, D, E, H, K, N, Q, R, S, and T
Positively charged residues H, K, and R
Small residues A, C, D, G, N, P, S, T, and V
Very small residues A, G, and S
Residues involved in turn A, C, D, E, G, H, K, N, Q, R, S, P, and formation T
Flexible residues Q, T, K, S, G, P, D, E, and R More conservative substitutions groupings include: valine-leucine-isoleucine, phenylalanine-tyrosine, lysine-arginine, alanine-valine, and asparagine-glutamine. Conservation in terms of hydropathic/hydrophilic properties and residue weight/size also is substantially retained in a variant CDR as compared to a CDR of [Ab name]. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The retention of similar residues may also or alternatively be measured by a similarity score, as determined by use of a BLAST program (e.g., BLAST 2.2.8 available through the NCBI using standard settings BLOSUM62, Open Gap=1 1 and Extended Gap=1). Suitable variants typically exhibit at least about 70% of identity to the parent peptide. According to the present invention a first amino acid sequence having at least 70% of identity with a second amino acid sequence means that the first sequence has 70; 71; 72; 73; 74; 75; 76; 77; 78; 79; 80; 81; 82; 83; 84;

85; 86; 87; 88; 89; 90; 91; 92; 93; 94; 95; 96; 97; 98; 99; or 100% of identity with the second amino acid sequence. According to the present invention a first amino acid sequence having at least 90% of identity with a second amino acid sequence means that the first sequence has 90; 91; 92; 93; 94; 95; 96; 97; 98; 99; or 100% of identity with the second amino acid sequence.

In some embodiments, the antibody of the present invention is an antibody having a heavy chain comprising i) the H-CDR1 of 14A5.2 mab, ii) the H-CDR2 of 14A5.2 mab and iii) the H-CDR3 of 14A5.2 mab and a light chain comprising i) the L-CDR1 of 14A5.2 mab, ii) the L-CDR2 of 14A5.2 mab and iii) the L-CDR3 of 14A5.2 mab.

In some embodiments, the antibody of the present invention is an antibody having a heavy chain having at least 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with SEQ ID NO:1 and a light chain having at least 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with SEQ ID NO:2.

In some embodiments, the antibody of the present invention is an antibody having a heavy chain identical to SEQ ID NO:1 and a light chain identical to SEQ ID NO:2.

In a particular embodiment, the antibodies described above bind to the same antigen and have the same properties of the antibody of the invention i.e. the antibody with the VH and VL of SEQ ID NO: 1 and 2.

Antibody which Compete with the Antibody of the Invention

In another aspect, the invention provides an antibody that competes for binding to Nectin-4 with the antibody of the invention.

As used herein, the term "binding" in the context of the binding of an antibody to a predetermined antigen or epitope typically is a binding with an affinity corresponding to a KD of about 10-7 M or less, such as about 10-8 M or less, such as about 10-9 M or less, about 10-10 M or less, or about 10-11 M or even less when determined by for instance surface plasmon resonance (SPR) technology in a BIAcore 3000 instrument using a soluble form of the antigen as the ligand and the antibody as the analyte. BIACORE® (GE Healthcare, Piscaataway, N.J.) is one of a variety of surface plasmon resonance assay formats that are routinely used to epitope bin panels of monoclonal antibodies. Typically, an antibody binds to the predetermined antigen with an affinity corresponding to a KD that is at least ten-fold lower, such as at least 100-fold lower, for instance at least 1,000-fold lower, such as at least 10,000-fold lower, for instance at least 100,000-fold lower than its KD for binding to a non-specific antigen (e.g., BSA, casein), which is not identical or closely related to the predetermined antigen. When the KD of the antibody is very low (that is, the antibody has a high affinity), then the KD with which it binds the antigen is typically at least 10,000-fold lower than its KD for a non-specific antigen. An antibody is said to essentially not bind an antigen or epitope if such binding is either not detectable (using, for example, plasmon resonance (SPR) technology in a BIAcore 3000 instrument using a soluble form of the antigen as the ligand and the antibody as the analyte), or is 100 fold, 500 fold, 1000 fold or more than 1000 fold less than the binding detected by that antibody and an antigen or epitope having a different chemical structure or amino acid sequence.

Additional antibodies can be identified based on their ability to cross-compete (e.g., to competitively inhibit the binding of, in a statistically significant manner) with other antibodies of the invention in standard Nectin-4 binding assays. The ability of a test antibody to inhibit the binding of antibodies of the present invention to Nectin-4 demonstrates that the test antibody can compete with that antibody for binding to Nectin-4; such an antibody may, according to non-limiting theory, bind to the same or a related (e.g., a structurally similar or spatially proximal) epitope on Nectin-4 as the antibody with which it competes. Thus, another aspect of the invention provides antibodies that bind to the same antigen as, and compete with, the antibodies disclosed herein. As used herein, an antibody "competes" for binding when the competing antibody inhibits nectin-4 binding of an antibody or antigen binding fragment of the invention by more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% in the presence of an equimolar concentration of competing antibody.

In other embodiments the antibodies or antigen binding fragments of the invention bind to one or more epitopes of Nectin-4. In some embodiments, the epitopes to which the present antibodies or antigen binding fragments bind are linear epitopes. In other embodiments, the epitopes to which the present antibodies or antigen binding fragments bind are non-linear, conformational epitopes.

The antibodies of the invention may be assayed for specific binding by any method known in the art. Many different competitive binding assay format(s) can be used for epitope binding. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York).

Antibody Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell-epitopes to thereby reduce the potential immunogenicity of the antibody. This approach is also referred to as "deimmunization"

and is described in further detail in U.S. Patent Publication No. 20030153043 by Carr et al.

In some embodiments, the glycosylation of an antibody is modified. Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

In some embodiments, some mutations are made to the amino acids localized in aggregation "hotspots" within and near the first CDR (CDR1) to decrease the antibodies susceptibility to aggregation (see Joseph M. Perchiacca et al., Proteins 2011; 79:2637-2647).

The antibody of the present invention may be of any isotype. The choice of isotype typically will be guided by the desired effector functions. IgG1 and IgG3 are isotypes that mediate such effectors functions as ADCC or CDC, when IgG2 and IgG4 don't or in a lower manner. Either of the human light chain constant regions, kappa or lambda, may be used. If desired, the class of a monoclonal antibody of the present invention may be switched by known methods. Typical, class switching techniques may be used to convert one IgG subclass to another, for instance from IgG1 to IgG2. Thus, the effector function of the monoclonal antibodies of the present invention may be changed by isotype switching to, e.g., an IgG1, IgG2, IgG3, IgG4, IgD, IgA, IgE, or IgM antibody for various therapeutic uses.

In some embodiments, the antibody of the present invention is a full-length antibody. In some embodiments, the full-length antibody is an IgG1 antibody. In some embodiments, the full-length antibody is an IgG3 antibody.

In some embodiments, the antibody of the present invention is an antibody of a non-IgG2/4 type, e.g. IgG1 or IgG3 which has been mutated such that the ability to mediate effector functions, such as ADCC, has been reduced or even eliminated. Such mutations have e.g. been described in Dall'Acqua W F et al., J Immunol. 177(2): 1129-1138 (2006) and Hezareh M, J Virol. 75(24): 12161-12168 (2001).

In some embodiments, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In some embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In some embodiments, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by ldusogie et al.

In some embodiments, one or more amino acid residues are altered to thereby alter the ability of the antibody to fix complement. This approach is described further in PCT Publication WO 94/29351 by Bodmer et al.

In some embodiments, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on human IgGI for FcγRI, FcγRII, FcγRIII and FcRn have been mapped and variants with improved binding have been described (see Shields, R. L. et al., 2001 J. Biol. Chen. 276:6591-6604, WO2010106180).

The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present invention to thereby produce an antibody with altered glycosylation. For example, EP1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in some embodiments, the monoclonal antibodies of the present invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields, R. L. et al, 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyl-transferase III (GnTIII)) such that antibodies expressed in the engineered cell lines exhibit increased bisecting GlcNac structures which results in increased ADCC activity of the antibodies (see also Umana et al, 1999 Nat. Biotech. 17: 176-180). Eureka Therapeutics further describes genetically engineered CHO mammalian cells capable of producing antibodies with altered mammalian glycosylation pattern devoid of fucosyl residues (http://www.eurekainc.com/ a&boutus/companyoverview.html). Alternatively, the monoclonal antibodies of the present invention can be produced in yeasts or filamentous fungi engineered for mammalian-like glycosylation pattern and capable of producing antibodies lacking fucose as glycosylation pattern (see for example EP1297172B1).

In another embodiment, the antibody is modified to increase its biological half-life. Various approaches are possible. For example, one or more of the following mutations can be introduced: T252L, T254S, T256F, as described in U.S. Pat. No. 6,277,375 by Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Antibodies with increased half lives and improved binding to the neonatal Fc receptor (FcRn), which is responsible for the transfer of maternal IgGs to the foetus (Guyer et al., J. Immunol. 117:587 (1976) and Kim et al., J. immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424, or 434, e.g., substitutions of Fc region residue 434 (U.S. Pat. No. 7,371,826).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP0154316 by Nishimura et al. and EP0401384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP0322094. Another possibility is a fusion of at least the antigen-binding region of the antibody of the invention to proteins capable of binding to serum proteins, such human serum albumin to increase half-life of the resulting molecule. Such approach is for example described in Nygren et al., EP 0 486 525.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In certain embodiments of the invention antibodies have been engineered to remove sites of deamidation. Deamidation is known to cause structural and functional changes in a peptide or protein. Deamidation can result in decreased bioactivity, as well as alterations in pharmacokinetics and antigenicity of the protein pharmaceutical. (Anal Chem. 2005 Mar. 1; 77(5):1432-9).

In certain embodiments of the invention the antibodies have been engineered to increase pI and improve their drug-like properties. The pI of a protein is a key determinant of the overall biophysical properties of a molecule. Antibodies that have low pIs have been known to be less soluble, less stable, and prone to aggregation. Further, the purification of antibodies with low pI is challenging and can be problematic especially during scale-up for clinical use. Increasing the pI of the anti-Nectin-4 antibodies of the invention or fragments thereof improved their solubility, enabling the antibodies to be formulated at higher concentrations (>100 mg/ml). Formulation of the antibodies at high concentrations (e.g. >100 mg/ml) offers the advantage of being able to administer higher doses of the antibodies into eyes of patients via intravitreal injections, which in turn may enable reduced dosing frequency, a significant advantage for treatment of chronic diseases including cardiovascular disorders. Higher pIs may also increase the FcRn-mediated recycling of the IgG version of the antibody thus enabling the drug to persist in the body for a longer duration, requiring fewer injections. Finally, the overall stability of the antibodies is significantly improved due to the higher pi resulting in longer shelf-life and bioactivity in vivo. Preferably, the pI is greater than or equal to 8.2.

Glycosylation modifications can also induce enhanced anti-inflammatory properties of the antibodies by addition of sialylated glycans. The addition of terminal sialic acid to the Fc glycan reduces FcγR binding and converts IgG antibodies to anti-inflammatory mediators through the acquisition of novel binding activities (see Robert M. Anthony et al., J Clin Immunol (2010) 30 (Suppl 1):S9-S14; Kai-Ting C et al., Antibodies 2013, 2, 392-414).

Antibody Mimetics

In some embodiments, the heavy and light chains, variable regions domains and CDRs that are disclosed can be used to prepare polypeptides that contain antigen binding region that can specifically bind to Nectin-4. For example, the CDRs of the 14A5.2 mab can be incorporated into a molecule (e.g., a polypeptide) covalently or noncovalently to make an immunoadhesion. An immunoadhesion may incorporate the CDRs as part of a larger polypeptide chain, may covalently link the CDRs to another polypeptide chain, or may incorporate the CDRs noncovalently. The CDRs enable the immunoadhesion to bind specifically to a particular antigen of interest (e.g., nectin-4 or epitope thereof).

The terms "polypeptide" and "protein" are used interchangeably herein to refer to a polymer of amino acid residues. The terms apply to amino acid polymers in which one or more amino acid residues is an artificial chemical mimetic of a corresponding naturally occurring amino acid, as well to naturally occurring amino acids polymers and non-naturally occurring amino acid polymers. Unless otherwise indicated, a particular polypeptide sequence also implicitly encompasses conservatively modified variants thereof.

In some embodiments, the antigen biding fragment of the invention is grafted into non-immunoglobulin based antibodies also called antibody mimetics selected from the group consisting of an affibody, an affilin, an affitin, an adnectin, an atrimer, an evasin, a DARPin, an anticalin, an avimer, a fynomer, and a versabody.

The term "antibody mimetic" is intended to refer to molecules capables of mimicking an antibody's ability to bind an antigen, but which are not limited to native antibody structures. Examples of such antibody mimetics include, but are not limited to, Adnectins, Affibodies, DARPins, Anticalins, Avimers, and versabodies, all of which employ binding structures that, while they mimic traditional antibody binding, are generated from and function via distinct mechanisms. Antigen biding fragments of antibodies can be grafted into scaffolds based on polypeptides such as Fibronectin type III (Fn3) (see U.S. Pat. No. 6,703,199, which describes fibronectin polypeptide monobodies). An affibody is well known in the art and refers to affinity proteins based on a 58 amino acid residue protein domain, derived from one of the IgG binding domain of staphylococcal protein A. DARPins (Designed Ankyrin Repeat Proteins) are well known in the art and refer to an antibody mimetic DRP (designed repeat protein) technology developed to exploit the binding abilities of non-antibody proteins. Anticalins are well known in the art and refer to another antibody mimetic technology, wherein the binding specificity is derived from lipocalins. Anticalins may also be formatted as dual targeting protein, called Duocalins. Avimers are well known in the art and refer to another antibody mimetic technology, Avimers are derived from natural A-domain containing protein. Versabodies are well known in the art and refer to another antibody mimetic technology, they are small proteins of 3-5 kDa with >15% cysteines, which form a high disulfide density scaffold, replacing the hydrophobic core the typical proteins have. Such antibody mimetic can be comprised in a scaffold. The term "scaffold" refers to a polypeptide platform for the engineering of new products with tailored functions and characteristics.

In one aspect, the invention pertains to generating non-immunoglobulin based antibodies also called antibody mimetics using non-immunoglobulins scaffolds onto which CDRs of the invention can be grafted. Known or future non-immunoglobulin frameworks and scaffolds may be employed, as long as they comprise a binding region specific for the target Nectin-4 protein.

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprise the entire antigen recognition unit in camel and llama IgG. Because of this structure, the non-immunoglobulin antibody mimics antigen binding properties that are similar in nature and affinity to those of antibodies. These scaffolds can be used in a loop randomisation and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The Ankyrin technology is based on using proteins with Ankyrin derived repeat modules as scaffolds for bearing variable regions which can be used for binding to different targets. The Ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on "A-domains" monomers (2-10) linked via amino acids linkers. Avimers can be created that can bind to the target antigen using the methodology described in, for example, U.S. patent Application publication Nos. 20040175756; 20050053973; 20050048512; and 20060008844.

Affibody affinity ligands are small, simple proteins composed of a three-helix bundle based on the scaffold of one of the IgG-binding domains of protein A. protein A is a surface protein form the bacterium *Staphylococcus aureus*. This scaffold domain consist of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acids residues, being just marginally bigger than a single immunoglobulin domain. The set of four loops, which makes up the binding pocket, shows pronounced structural plasticity and tolerates a variety of side chains. The binding site can can thus be reshaped in a proprietary process in order to recognize prescribed target molecules of different shape with high affinity and specificity. One protein of lipocalin family, the bilin-binding protein (BBP) of Pieris Brassicae has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of "ubiquitin-like" proteins are described in WO2004106368.

Versabodies are highly soluble and can be formulated to high concentrations. Versabodies are exceptionally heat stable and offer extended shelf-life. Additional information regarding Versabodies can be found in US 2007/0191272, which is hereby incorporated by reference in its entirety.

The above descriptions of antibody fragment and mimetic technologies is not intended to be comprehensive. A variety of additional technologies including alternative polypeptide-based technologies, such as fusions of complementarity determining regions as outlined in Qui et al., Nature Biotechnology, 25(8) 921-929 (2007), as well as nucleic acid-based technologies, such as the RNA aptamer technologies described in U.S. Pat. Nos. 5,789,157; 5,864,026; 5,712,375; 5,763,566; 6,013,443; 6,376,474; 6,613,526; 6,114,120; 6,261,774; and 6,387,620; all of which are hereby incorporated by reference, could be used in the context of the instant invention.

CAR-T Cells

The present invention also provides chimeric antigen receptors (CARs) comprising an antigen binding domain of the antibody of the present invention. Typically, said chimeric antigen receptor comprises at least one VH and/or VL sequence of the antibody of the present invention. The chimeric antigen receptor of the present invention also comprises an extracellular hinge domain, a transmembrane domain, and an intracellular T cell signaling domain.

As used herein, the term "chimeric antigen receptor" or "CAR" has its general meaning in the art and refers to an artificially constructed hybrid protein or polypeptide containing the antigen binding domains of an antibody (e.g., scFv) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

In some embodiments, the invention provides CARs comprising an antigen-binding domain comprising, consisting of, or consisting essentially of, a single chain variable fragment (scFv) of the 14A5.2 mab. In some embodiments, the antigen binding domain comprises a linker peptide. The linker peptide may be positioned between the light chain variable region and the heavy chain variable region.

In some embodiments, the CAR comprises an extracellular hinge domain, a transmembrane domain, and an intracellular T cell signaling domain selected from the group consisting of CD28, 4-1BB, and CD3ζ intracellular domains. CD28 is a T cell marker important in T cell co-stimulation. 4-1BB transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs).

In some embodiments, the chimeric antigen receptor of the present invention can be glycosylated, amidated, carboxylated, phosphorylated, esterified, N-acylated, cyclized via, e.g., a disulfide bridge, or converted into an acid addition salt and/or optionally dimerized or polymerized.

The invention also provides a nucleic acid encoding for a chimeric antigen receptor of the present invention. In some embodiments, the nucleic acid is incorporated in a vector as such as described above.

The present invention also provides a host cell comprising a nucleic acid encoding for a chimeric antigen receptor of the present invention. While the host cell can be of any cell type, can originate from any type of tissue, and can be of any developmental stage; the host cell is a T cell, e.g. isolated from peripheral blood lymphocytes (PBL) or peripheral blood mononuclear cells (PBMC). In some embodiments, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell can be any type of T cell and can be of any developmental stage, including but not limited to, CD4+/CD8+ double positive T cells, CD4+ helper T cells, e.g., Th2 cells, CD8+ T cells (e.g., cytotoxic T cells), tumor infiltrating cells, memory T cells, naive T cells, and the like. The T cell may be a CD8+ T cell or a CD4+ T cell.

The population of those T cells prepared as described above can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg. Adoptive immunotherapy of cancer refers to a therapeutic approach in which immune cells with an antitumor reactivity are administered to a tumor-bearing host, with the aim that the cells mediate either directly or indirectly, the regression of an established tumor. Transfusion of lymphocytes, particularly T lymphocytes, falls into this category. Currently, most adoptive immunotherapies are autolymphocyte therapies (ALT) directed to treatments using the patient's own immune cells. These therapies involve processing the patient's own lymphocytes to either enhance the immune cell mediated response or to recognize specific antigens or foreign substances in the body, including the cancer cells. The treatments are accomplished by removing the patient's lymphocytes and exposing these cells in vitro to biologics and drugs to activate the immune function of the cells. Once the autologous cells are activated, these ex vivo activated cells are reinfused into the patient to enhance the immune system to treat cancer. In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin. A treatment-effective amount of cells in the composition is dependent on the relative representation of the T cells with the desired specificity, on the age and weight of the recipient, on the severity of the targeted condition and on the immunogenicity of the targeted Ags. These amount of cells can be as low as approximately $10^3$/kg, preferably $5 \times 10^3$/kg; and as high as $10^7$/kg, preferably $10^8$/kg. The number of cells will depend upon the ultimate use for which the composition is intended, as will the type of cells included therein. For example, if cells that are specific for a particular Ag are desired, then the population will contain greater than 70%, generally greater than 80%, 85% and 90-95% of such cells. For uses provided herein, the cells are generally in a volume of a liter or less, can be 500 ml or less, even 250 ml or 100 ml or less. The clinically relevant number of immune cells can be apportioned into multiple infusions that cumulatively equal or exceed the desired total amount of cells.

In particular the cells of the present invention are particularly suitable for the treatment of cancer. Accordingly, a further object of the present invention relates to a method of treating cancer in a subject in need thereof comprising administering to the subject a therapeutically effective amount of a population of cells of the present invention.

Multispecific Antibodies

In some embodiments, the invention provides a multispecific antibody comprising a first antigen binding site from an antibody of the present invention molecule described herein above and at least one second antigen binding site.

In some embodiments, the second antigen-binding site is used for recruiting a killing mechanism such as, for example, by binding an antigen on a human effector cell as a BiTE (Bispecific T-Cell engager) antibody which is a bispecific scFv2 directed against target antigen and CD3 on T cells described in U.S. Pat. No. 7,235,641, or by binding a cytotoxic agent or a second therapeutic agent. As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, mast cells and granulocytes, such as neutrophils, eosinophils and basophils. Some effector cells express specific Fc receptors (FcRs) and carry out specific immune functions. In some embodiments, an effector cell is capable of inducing ADCC, such as a natural killer cell. For example, monocytes, macrophages, which express FcRs, are involved in specific killing of target cells and presenting antigens to other components of the immune system. In some embodiments, an effector cell may phagocytose a target antigen or target cell. The expression of a particular FcR on an effector cell may be regulated by humoral factors such as cytokines. An effector cell can phagocytose a target antigen or phagocytose or lyse a target cell. Suitable cytotoxic agents and second therapeutic agents are exemplified below, and include toxins (such as radiolabeled peptides), chemotherapeutic agents and prodrugs In some embodiments, the second antigen-binding site binds to an antigen on a human B cell, such as, e.g., CD19, CD20, CD21, CD22, CD23, CD46, CD80, CD138 and HLA-DR.

In some embodiments, the second antigen-binding site binds a tissue-specific antigen, promoting localization of the bispecific antibody to a specific tissue.

In some embodiments, the second antigen-binding site binds to an antigen located on the same type of cell as the Nectin-4-expressing cell, typically a tumor-associated antigen (TAA), but has a binding specificity different from that of the first antigen-binding site. Such multi- or bispecific antibodies can enhance the specificity of the tumor cell binding and/or engage multiple effector pathways. Exemplary TAAs include carcinoembryonic antigen (CEA), prostate specific antigen (PSA), RAGE (renal antigen), a-fetoprotein, CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, c-Met, Marti, MelanA, MUM-1, MUM-2, MUM-3, HLA-B7, Ep-CAM or a cancer-associated integrin, such as α5β3 integrin. Alternatively, the second antigen-binding site binds to a different epitope of [antigen]. The second antigen-binding site may alternatively bind an angiogenic factor or other cancer-associated growth factor, such as a vascular endothelial growth factor, a fibroblast growth factor, epidermal growth factor, angiogenin or a receptor of any of these, particularly receptors associated with cancer progression.

In some embodiments, the second antigen-binding site is from a second antibody or ADC of the invention, such as the antibody of the present invention.

Exemplary formats for the multispecific antibody molecules of the invention include, but are not limited to (i) two antibodies cross-linked by chemical heteroconjugation, one with a specificity to [antigen] and another with a specificity to a second antigen; (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')2 fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fab-arm; and (x) a diabody. Another exemplary format for bispecific antibodies is IgG-like molecules with complementary CH3 domains to force heterodimerization. Such molecules can be prepared using known technologies, such as, e.g., those known as Triomab/Quadroma (Trion Pharma/Fresenius Biotech), Knob-into-Hole (Genentech), CrossMAb (Roche) and electrostatically-matched (Amgen), LUZ-Y (Genentech), Strand Exchange Engineered Domain body (SEEDbody) (EMD Serono), Biclonic (Merus) and DuoBody (Genmab A/S) technologies.

In some embodiments, the bispecific antibody is obtained or obtainable via a controlled Fab-arm exchange, typically using DuoBody technology. In vitro methods for producing bispecific antibodies by controlled Fab-arm exchange have been described in WO2008119353 and WO 2011131746 (both by Genmab A/S). In one exemplary method, described in WO 2008119353, a bispecific antibody is formed by "Fab-arm" or "half-molecule" exchange (swapping of a heavy chain and attached light chain) between two monospecific antibodies, both comprising IgG4-like CH3 regions, upon incubation under reducing conditions. The resulting product is a bispecific antibody having two Fab arms which may comprise different sequences. In another exemplary method, described in WO 2011131746, bispecific antibodies of the present invention are prepared by a method comprising the following steps, wherein at least one of the first and second antibodies is the antibody of the present invention: a) providing a first antibody comprising an Fc region of an immunoglobulin, said Fc region comprising a first CH3 region; b) providing a second antibody comprising an Fc region of an immunoglobulin, said Fc region comprising a second CH3 region; wherein the sequences of said first and second CH3 regions are different and are such that the heterodimeric interaction between said first and second CH3 regions is stronger than each of the homodimeric interactions of said first and second CH3 regions; c) incubating said first antibody together with said second antibody under reducing conditions; and d) obtaining said bispecific antibody, wherein the first antibody is the antibody of the present invention and the second antibody has a different binding specificity, or vice versa. The reducing conditions may, for example, be provided by adding a reducing agent, e.g. selected from 2-mercaptoethylamine, dithiothreitol and tris(2-carboxyethyl)phosphine. Step d) may further comprise restoring the conditions to become non-reducing or less reducing, for example by removal of a reducing agent, e.g. by desalting. Preferably, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety. The following are exemplary embodiments of combinations of such asymmetrical mutations, optionally wherein one or both Fc-regions are of the IgG1 isotype.

In some embodiments, the first Fc region has an amino acid substitution at a position selected from the group consisting of: 366, 368, 370, 399, 405, 407 and 409, and the second Fc region has an amino acid substitution at a position selected from the group consisting of: 366, 368, 370, 399, 405, 407 and 409, and wherein the first and second Fc regions are not substituted in the same positions.

In some embodiments, the first Fc region has an amino acid substitution at position 405, and said second Fc region has an amino acid substitution at a position selected from the group consisting of: 366, 368, 370, 399, 407 and 409, optionally 409.

In some embodiments, the first Fc region has an amino acid substitution at position 409, and said second Fc region has an amino acid substitution at a position selected from the group consisting of: 366, 368, 370, 399, 405, and 407, optionally 405 or 368.

In some embodiments, both the first and second Fc regions are of the IgG1 isotype, with the first Fc region having a Leu at position 405, and the second Fc region having an Arg at position 409.

Immunoconjugates

An antibody of the invention can be conjugated with a detectable label to form an anti-Nectin-4 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below. The detectable label can be a radioisotope that is detected by autoradiography. Isotopes that are particularly useful for the purpose of the invention are 3H, 125I, 131I, 35S and 14C.

Anti-Nectin-4 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-Nectin-4 immunoconjugates can be detectably labeled by coupling an antibody to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-nectin-4 immunoconjugates of the invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-Nectin-4 immunoconjugates can be detectably labeled by linking an anti-[antigen] antibody to an enzyme. When the anti-Nectin-4-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the invention. The binding of marker moieties to anti-Nectin-4 monoclonal antibodies can be accomplished using standard techniques known to the art. Typical methodology in this regard is described by Kennedy et al., Clin. Chim. Acta 70:1, 1976; Schurs et al., Clin. Chim. Acta 81:1, 1977; Shih et al., Int'l J. Cancer 46:1101, 1990; Stein et al., Cancer Res. 50:1330, 1990; and Coligan, supra.

Moreover, the convenience and versatility of immunochemical detection can be enhanced by using anti-Nectin-4 monoclonal antibodies that have been conjugated with avidin, streptavidin, and biotin. (See, e.g., Wilchek et al. (eds.), "Avidin-Biotin Technology," Methods In Enzymology (Vol. 184) (Academic Press 1990); Bayer et al., "Immunochemical Applications of Avidin-Biotin Technology," in Methods In Molecular Biology (Vol. 10) 149-162 (Manson, ed., The Humana Press, Inc. 1992).)

Methods for performing immunoassays are well-established. (See, e.g., Cook and Self, "Monoclonal Antibodies in Diagnostic Immunoassays," in Monoclonal Antibodies: Production, Engineering, and Clinical Application 180-208 (Ritter and Ladyman, eds., Cambridge University Press 1995); Perry, "The Role of Monoclonal Antibodies in the Advancement of Immunoassay Technology," in Monoclonal Antibodies: Principles and Applications 107-120 (Birch and Lennox, eds., Wiley-Liss, Inc. 1995); Diamandis, Immunoassay (Academic Press, Inc. 1996).)

In some embodiments, the antibody of the present invention is conjugated to a therapeutic moiety, i.e. a drug. The therapeutic moiety can be, e.g., a cytotoxin, a chemotherapeutic agent, a cytokine, an immunosuppressant, an immune stimulator, a lytic peptide, or a radioisotope. Such conjugates are referred to herein as an "antibody-drug conjugates" or "ADCs".

In some embodiments, the antibody is conjugated to a cytotoxic moiety. The cytotoxic moiety may, for example, be selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor such as maytansine or an analog or derivative thereof; an antimitotic agent such as monomethyl auristatin E or F or an analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof; an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins such as PAPI, PAPII, and PAP-S, *Momordica charantia* inhibitor, curcin, crotin, *Sapaonaria officinalis* inhibitor, gelonin, mitogellin, restrictocin, phenomycin, and enomycin toxins; ribonuclease (RNase); DNase I, Staphylococcal enterotoxin A; pokeweed antiviral protein; diphtherin toxin; and *Pseudomonas* endotoxin.

In some embodiments, the antibody is conjugated to a nucleic acid or nucleic acid-associated molecule. In one such embodiment, the conjugated nucleic acid is a cytotoxic ribonuclease (RNase) or deoxy-ribonuclease (e.g., DNase I), an antisense nucleic acid, an inhibitory RNA molecule (e.g., a siRNA molecule) or an immunostimulatory nucleic acid (e.g., an immunostimulatory CpG motif-containing DNA molecule). In some embodiments, the antibody is conjugated to an aptamer or a ribozyme.

In some embodiments, the antibody is conjugated, e.g., as a fusion protein, to a lytic peptide such as CLIP, Magainin 2, mellitin, Cecropin and P18.

In some embodiments, the antibody is conjugated to a cytokine, such as, e.g., IL-2, IL-4, IL-6, IL-7, IL-10, IL-12, IL-13, IL-15, IL-18, IL-23, IL-24, IL-27, IL-28a, IL-28b, IL-29, KGF, IFNa, IFN3, IFNy, GM-CSF, CD40L, Flt3 ligand, stem cell factor, ancestim, and TNFa.

In some embodiments, the antibody is conjugated to a radioisotope or to a radioisotope-containing chelate. For example, the antibody can be conjugated to a chelator linker, e.g. DOTA, DTPA or tiuxetan, which allows for the antibody to be complexed with a radioisotope. The antibody may also or alternatively comprise or be conjugated to one or more radiolabeled amino acids or other radiolabeled molecules Non-limiting examples of radioisotopes include 3H, 14C, 15N, 35S, 90Y, 99Tc, 125I, 131I, 186Re, 213Bi, 225Ac and 227Th. For therapeutic purposes, a radioisotope emitting beta- or alpha-particle radiation can be used, e.g., 131I, 90Y, 211At, 212Bi, 67Cu, 186Re, 188Re, and 212Pb.

In certain embodiments, an antibody-drug conjugate comprises an anti-tubulin agent. Examples of anti-tubulin agents include, for example, taxanes (e.g., Taxol® (paclitaxel), Taxotere® (docetaxel)), T67 (Tularik), vinca alkyloids (e.g., vincristine, vinblastine, vindesine, and vinorelbine) and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of anti-tubulin agents. For example, in specific embodiments, the maytansinoid is maytansine or DM-1 (ImmunoGen, Inc.; see also Chari et al., Cancer Res. 52:127-131, 1992).

In other embodiments, the cytotoxic agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, an anti-Nectin-4 antibody is conjugated to a pro-drug converting enzyme. The pro-drug converting enzyme can be recombinantly fused to the antibody or chemically conjugated thereto using known methods. Exemplary pro-drug converting enzymes are carboxypeptidase G2, β-glucuronidase, penicillin-V-amidase, penicillin-G-amidase, β-lactamase, β-glucosidase, nitroreductase and carboxypeptidase A.

Other molecule using as therapeutic moiety can be PyrroloBenzoDiazepine dimers (PBD).

In a particular embodiment, the antibody is a chimeric antibody having a heavy chain identical to SEQ ID NO:1 and a light chain identical to SEQ ID NO:2 and conjugated to the MMAE.

In another particular embodiment, the antibody is a chimeric antibody having a heavy chain identical to SEQ ID NO:1 and a light chain identical to SEQ ID NO:2 and conjugated to PyrroloBenzoDiazepine dimers (PBD).

Typically, the antibody-drug conjugate compounds comprise a linker unit between the drug unit and the antibody unit. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123).

Most typical are peptidyl linkers that are cleavable by enzymes that are present in 191P4D12-expressing cells. Examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the Val-Cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values.

Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene), SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation.

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of antibody-drug conjugate compound, are cleaved when the antibody-drug conjugate compound is present in an extracellular environment (e.g., in plasma). Whether a linker is not substantially sensitive to the extracellular environment can be determined, for example, by incubating with plasma the antibody-drug conjugate compound for a predetermined time period (e.g., 2, 4, 8, 16, or 24 hours) and then quantitating the amount of free drug present in the plasma.

Techniques for conjugating molecules to antibodies, are well-known in the art (See, e.g., Arnon et al., "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al., "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radio labeled Antibody In Cancer Therapy," in Monoclonal Antibodies For Cancer Detection And Therapy (Baldwin et al. eds., Academic Press, 1985); and Thorpe et al., 1982, Immunol. Rev. 62:119-58. See also, e.g., PCT publication WO 89/12624.) Typically, the nucleic acid molecule is covalently attached to lysines or cysteines on the antibody, through N-hydroxysuccinimide ester or maleimide functionality respectively. Methods of conjugation using engineered cysteines or incorporation of unnatural amino acids have been reported to improve the homogeneity of the conjugate (Axup, J. Y., Bajjuri, K. M., Ritland, M., Hutchins, B. M., Kim, C. H., Kazane, S. A., Halder, R., Forsyth, J. S., Santidrian, A. F., Stafin, K., et al. (2012). Synthesis of site-specific antibody-drug conjugates using unnatural amino acids. Proc. Natl. Acad. Sci. USA 109, 16101-16106.; Junutula, J. R., Flagella, K. M., Graham, R. A., Parsons, K. L., Ha, E., Raab, H., Bhakta, S., Nguyen, T., Dugger, D. L., Li, G., et al. (2010). Engineered thiotrastuzumab-DM1 conjugate with an improved therapeutic index to target humanepidermal growth factor receptor 2-positive breast cancer. Clin. Cancer Res. 16, 4769-4778.). Junutula et al. (2008) developed cysteine-based site-specific conjugation called "THIOMABs" (TDCs) that are claimed to display an improved therapeutic index as compared to conventional conjugation methods. Conjugation to unnatural amino acids that have been incorporated into the antibody is also being explored for ADCs; however, the generality of this approach is yet to be established (Axup et al., 2012). In particular the one skilled in the art can also envisage Fc-containing polypeptide engineered with an acyl donor glutamine-containing tag (e.g., Gln-containing peptide tags or Q-tags) or an endogenous glutamine that are made reactive by polypeptide engineering (e.g., via amino acid deletion, insertion, substitution, or mutation on the polypeptide). Then a transglutaminase, can covalently crosslink with an amine donor agent (e.g., a small molecule comprising or attached to a reactive amine) to form a stable and homogenous population of an engineered Fc-containing polypeptide conjugate with the amine donor agent being site-specifically conjugated to the Fc-containing polypeptide through the acyl donor glutamine-containing tag or the accessible/exposed/reactive endogenous glutamine (WO 2012059882).

Diagnostic and Therapeutic Uses

A further aspect of the invention relates to the anti-Nectin-4 antibody of the invention for diagnosing and/or monitoring and/or staging a cancer and particularly a cancer in which Nectin-4 is overexpressed.

According to the invention, a cancer in which Nectin-4 is overexpressed denotes a cancer with a level of nectin-4 expressed at the surface of the cancerous cells superior to the level of Nectin-4 expressed by normal cells (non tumoral cells).

According to the invention, cancers in which Nectin-4 is overexpression are modified can be breast, ovarian, lung, urothelial and pancreatic cancers. In one embodiment, the breast cancer is triple negative breast cancer.

In a preferred embodiment, antibodies of the invention may be labelled with a detectable molecule or substance, such as a fluorescent molecule, a radioactive molecule or any others labels known in the art as above described. For example, an antibody of the invention may be labelled with a radioactive molecule by any method known to the art. For example radioactive molecules include but are not limited radioactive atom for scintigraphic studies such as I123, I124, In111, Re186, Re188. Antibodies of the invention may be also labelled with a spin label for nuclear magnetic resonance (NMR) imaging (also known as magnetic resonance imaging, MRI), such as iodine-123, iodine-131, indium-111, fluorine-19, carbon-13, nitrogen-15, oxygen-17, gadolinium, manganese or iron. Following administration of the antibody, the distribution of the antibody within the patient is detected. Methods for detecting distribution of any specific label are known to those skilled in the art and any appropriate method can be used. Some non-limiting examples include, computed tomography (CT), position emission tomography (PET), magnetic resonance imaging (MRI), fluorescence, chemiluminescence and sonography.

Typically, said diagnostic methods involve the use of a biological sample obtained from the patient. As used herein the term "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. For example, biological samples include cells obtained from a tissue sample collected from an individual suspected of having a cancer associated with Nectin-4 overexpression, and in a preferred embodiment from breast, ovarian, lung, urothelial and pancreatic cancers.

Therefore, biological samples encompass clinical samples, cancer samples, cells in culture, cell supernatants, cell lysates, serum, plasma, biological fluid, and tissue samples.

Antibodies, fragments or immunoconjugates of the invention may be useful for treating any disease associated with Nectin-4 overexpression particularly cancers and metastatic cancers.

The antibodies of the invention may be used alone or in combination with any suitable agent.

In each of the embodiments of the treatment methods described herein, the anti-nectin-4 antibody or anti-nectin-4 antibody-drug conjugate is delivered in a manner consistent with conventional methodologies associated with management of the disease or disorder for which treatment is sought. In accordance with the disclosure herein, an effective amount of the antibody or antibody-drug conjugate is administered to a patient in need of such treatment for a time and under conditions sufficient to prevent or treat the disease or disorder.

As used herein, the terms "treatment" and "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "therapeutically effective amount" or "effective amount" refers to an amount effective, at dosages and for periods of time necessary, to achieve a desired therapeutic result. A therapeutically effective amount of the antibody of the present invention may vary according to factors such as the disease state, age, sex, and weight of the individual, and the ability of the antibody of the present invention to elicit a desired response in the individual. A therapeutically effective amount is also one in which any toxic or detrimental effects of the antibody or antibody portion are outweighed by the therapeutically beneficial effects. The efficient dosages and dosage regimens for the antibody of the present invention depend on the disease or condition to be treated and may be determined by the persons skilled in the art. A physician having ordinary skill in the art may readily determine and prescribe the effective amount of the pharmaceutical composition required. For example, the physician could start doses of the antibody of the present invention employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. Typically, the ability of a compound to inhibit cancer may, for example, be evaluated in an animal model system predictive of efficacy in human tumors. Alternatively, this property of a composition may be evaluated by examining the ability of the compound to induce cytotoxicity by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected. An exemplary, non-limiting range for a therapeutically effective amount of an antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. In some embodiments, the efficacy may be monitored by visualization of the disease area, or by other diagnostic methods described further herein, e.g. by performing one or more PET-CT scans, for example using a labeled antibody of the present invention, fragment or mini-antibody derived from the antibody of the present invention. If desired, an effective daily dose of a pharmaceutical composition may be administered as two, three, four, five, six or more sub-doses administered separately at appropriate intervals throughout the day, optionally, in unit dosage forms. In some embodiments, the monoclonal antibodies of the present invention are administered by slow continuous infusion over a long period, such as more than 24 hours, in order to minimize any unwanted side effects. An effective dose of an antibody of the present invention may also be administered using a weekly, biweekly or triweekly dosing period. The dosing period may be restricted to, e.g., 8 weeks, 12 weeks or until clinical progression has been established. As non-limiting examples, treatment according to the present invention may be provided as a daily dosage of an antibody of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Accordingly, one object of the present invention relates to a method of treating cancers and metastatic cancers in a subject in need thereof comprising administering to the subject a therapeutically effective amount of the antibody of the present invention.

In another aspect, the present invention relates to the antibody of the present invention, as defined in any aspect or embodiment herein, for use as a medicament.

In some embodiments, the subject suffers from a cancer. Accordingly, a further object of the present invention relates to a method of treating a cancer in a subject in need thereof comprising administering to the subject a therapeutically effective amount of the antibody of the present invention.

As used herein, the term "cancer" has its general meaning in the art and includes, but is not limited to, solid tumors and blood borne tumors The term cancer includes diseases of the skin, tissues, organs, bone, cartilage, blood and vessels. The term "cancer" further encompasses both primary and metastatic cancers. Examples of cancers that may treated by methods and compositions of the invention include, but are not limited to, cancer cells from the bladder, blood, bone, bone marrow, brain, breast, colon, esophagus, gastrointestinal, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malign melanoma in giant pigmented nevus; epithelioid cell melanoma; blue nevus, malignant; sarcoma; fibrosarcoma; fibrous histiocytoma, malignant; myxo sarcoma; liposarcoma; leiomyo sarcoma; rhabdomyo sarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangio sarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

More particularly, the invention is suitable to treat breast, ovarian, lung, urothelial and pancreatic cancers. In one embodiment, the breast cancer is a triple negative breast cancer.

In certain embodiments, an anti-nectin-4 antibody or antibody-drug conjugate is used in combination with a second agent for treatment of a disease or disorder. When used for treating cancer, an anti-Nectin-4 antibody or antibody-drug conjugate of the invention may be used in combination with conventional cancer therapies such as, e.g., surgery, radiotherapy, chemotherapy, or combinations thereof.

The present invention also provides for therapeutic applications where an antibody of the present invention is used in combination with at least one further therapeutic agent, e.g. for treating cancers and metastatic cancers. Such administration may be simultaneous, separate or sequential. For simultaneous administration the agents may be administered as one composition or as separate compositions, as appropriate. The further therapeutic agent is typically relevant for the disorder to be treated. Exemplary therapeutic agents include other anti-cancer antibodies, cytotoxic agents, chemotherapeutic agents, anti-angiogenic agents, anti-cancer immunogens, cell cycle control/apoptosis regulating agents, hormonal regulating agents, and other agents described below.

In some embodiments, the antibody of the present invention is used in combination with a chemotherapeutic agent. The term "chemotherapeutic agent" refers to chemical compounds that are effective in inhibiting tumor growth. Examples of chemotherapeutic agents include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalamycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid;

aceglatone; aldophosphamide glycoside; amino levulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.].) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit honnone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the antibody of the present invention is used in combination with a targeted cancer therapy. Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names. In some embodiments, the targeted therapy consists of administering the subject with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S. Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signaling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), MK-2206 (8-[4-aminocyclobutyl)phenyl]-9-phenyl-1,2,4-triazolo[3,4-f][1,6]naphthyridin-3(2H)-one hydrochloride) derivatives thereof, analogs thereof, and combinations thereof. Additional tyrosine kinase inhibitors and related compounds suitable for use in the present invention are described in, for example, U.S. Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In some embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the antibody of the present invention is used in combination with an immunotherapeutic agent. The term "immunotherapeutic agent," as used herein, refers to a compound, composition or treatment that indirectly or directly enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the subject with an amount of immune cells (T cells, NK, cells, dendritic cells, B cells . . . ). Immunotherapeutic agents can be non-specific, i.e. boost the immune system generally so that the human body becomes more effective in fighting the growth and/or spread of cancer cells, or they can be specific, i.e. targeted to the cancer cells themselves immunotherapy regimens may combine the use of non-specific and specific immunotherapeutic agents. Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants. A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors. Interferons (IFNs) contemplated by the present invention include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behavior and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation). Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention. Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin). Combination compositions and combination administration methods of the present invention may also involve "whole cell" and "adoptive" immunotherapy methods. For instance, such methods may comprise infusion or re-infusion of immune system cells (for instance tumor-infiltrating lymphocytes (TILs), such as CC2+ and/or CD8+ T cells (for instance T cells expanded with tumor-specific antigens and/or genetic enhancements), antibody-expressing B cells or other antibody-producing or -presenting cells, dendritic cells (e.g., dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include Canvaxin™, APC-8015 (Dendreon), HSPPC-96 (Antigenics), and Melacine® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions.

Particularly, the antibody of the invention may be used in combination with another antibody like the antibody Ha22-2 (Seattle Genetics) described in the patent application WO2012047724.

In some embodiments, the antibody of the present invention is used in combination with radiotherapy. Radiotherapy may comprise radiation or associated administration of radiopharmaceuticals to a patient. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the antibody of the present invention is used in combination with an antibody that is specific for a costimulatory molecule. Examples of antibodies that are specific for a costimulatory molecule include but are not limited to anti-CTLA4 antibodies (e.g. Ipilimumab), anti-PD1 antibodies, anti-PDLL antibodies, anti-TIMP3 antibodies, anti-LAG3 antibodies, anti-B7H3 antibodies, anti-B7H4 antibodies or anti-B7H6 antibodies.

In some embodiments, the second agent is an agent that induces, via ADCC, the death of a cell expressing an antigen to which the second agent binds. In some embodiments, the agent is an antibody (e.g. of IgG1 or IgG3 isotype) whose mode of action involves induction of ADCC toward a cell to which the antibody binds. NK cells have an important role in inducing ADCC and increased reactivity of NK cells can be directed to target cells through use of such a second agent. In some embodiments, the second agent is an antibody specific for a cell surface antigens, e.g., membrane antigens. In some embodiments, the second antibody is specific for a tumor antigen as described above (e.g., molecules specifically expressed by tumor cells), such as CD20, CD52, ErbB2 (or HER2/Neu), CD33, CD22, CD25, MUC-1, CEA, KDR, αVβ3, etc., particularly lymphoma antigens (e.g., CD20). Accordingly, the present invention also provides methods to enhance the anti-tumor effect of monoclonal antibodies directed against tumor antigen(s). In the methods of the invention, ADCC function is specifically augmented, which in turn enhances target cell killing, by sequential administration of an antibody directed against one or more tumor antigens, and an antibody of the present invention.

Accordingly, a further object relates to a method of enhancing NK cell antibody-dependent cellular cytotoxicity (ADCC) of an antibody in a subject in need thereof comprising administering to the subject the antibody, and administering to the subject an antibody of the present invention.

A further object of the present invention relates to a method of treating cancer in a subject in need thereof comprising administering to the subject a first antibody selective for a cancer cell antigen, and administering to the subject an antibody of the present invention.

A number of antibodies are currently in clinical use for the treatment of cancer, and others are in varying stages of clinical development. Antibodies of interest for the methods of the invention act through ADCC, and are typically selective for tumor cells, although one of skill in the art will recognize that some clinically useful antibodies do act on non-tumor cells, e.g. CD20. There are a number of antigens and corresponding monoclonal antibodies for the treatment of B cell malignancies. One popular target antigen is CD20, which is found on B cell malignancies. Rituximab is a chimeric unconjugated monoclonal antibody directed at the CD20 antigen. CD20 has an important functional role in B cell activation, proliferation, and differentiation. The CD52 antigen is targeted by the monoclonal antibody alemtuzumab, which is indicated for treatment of chronic lymphocytic leukemia. CD22 is targeted by a number of antibodies, and has recently demonstrated efficacy combined with toxin in chemotherapy-resistant hairy cell leukemia. Monoclonal antibodies targeting CD20, also include tositumomab and ibritumomab. Monoclonal antibodies useful in the methods of the invention, which have been used in solid tumors, include without limitation edrecolomab and trastuzumab (herceptin). Edrecolomab targets the 17-1 A antigen seen in colon and rectal cancer, and has been approved for use in Europe for these indications. Its antitumor effects are mediated through ADCC, CDC, and the induction of an anti-idiotypic network. Trastuzumab targets the HER-2/neu antigen. This antigen is seen on 25% to 35% of breast cancers. Trastuzumab is thought to work in a variety of ways: downregulation of HER-2 receptor expression, inhibition of proliferation of human tumor cells that overexpress HER-2 protein, enhancing immune recruitment and ADCC against tumor cells that overexpress HER-2 protein, and downregulation of angiogenesis factors. Alemtuzumab (Campath) is used in the treatment of chronic lymphocytic leukemia; colon cancer and lung cancer; Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer. Cetuximab (Erbitux) is also of interest for use in the methods of the invention. The antibody binds to the EGF receptor (EGFR), and has been used in the treatment of solid tumors including colon cancer and squamous cell carcinoma of the head and neck (SCCHN).

Pharmaceutical Compositions

Typically, the antibody of the present invention is administered to the subject in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a patient, the composition will be formulated for administration to the patient. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 mg/m2 and 500 mg/m2. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the invention for injection (e.g., intramuscular, i.v.) could be prepared to contain sterile buffered water (e.g. 1 ml for intramuscular), and between about 1 ng to about 100 mg, e.g. about 50 ng to about 30 mg or more preferably, about 5 mg to about 25 mg, of an anti-myosin 18A antibody of the invention.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The invention will be further illustrated by the following figures and examples. However, these examples and figures should not be interpreted in any way as limiting the scope of the present invention.

FIGURES

FIG. 1: Western-blot analysis of Nectin-4 expression using 14A5.2 monoclonal antibody.

Figure 2:
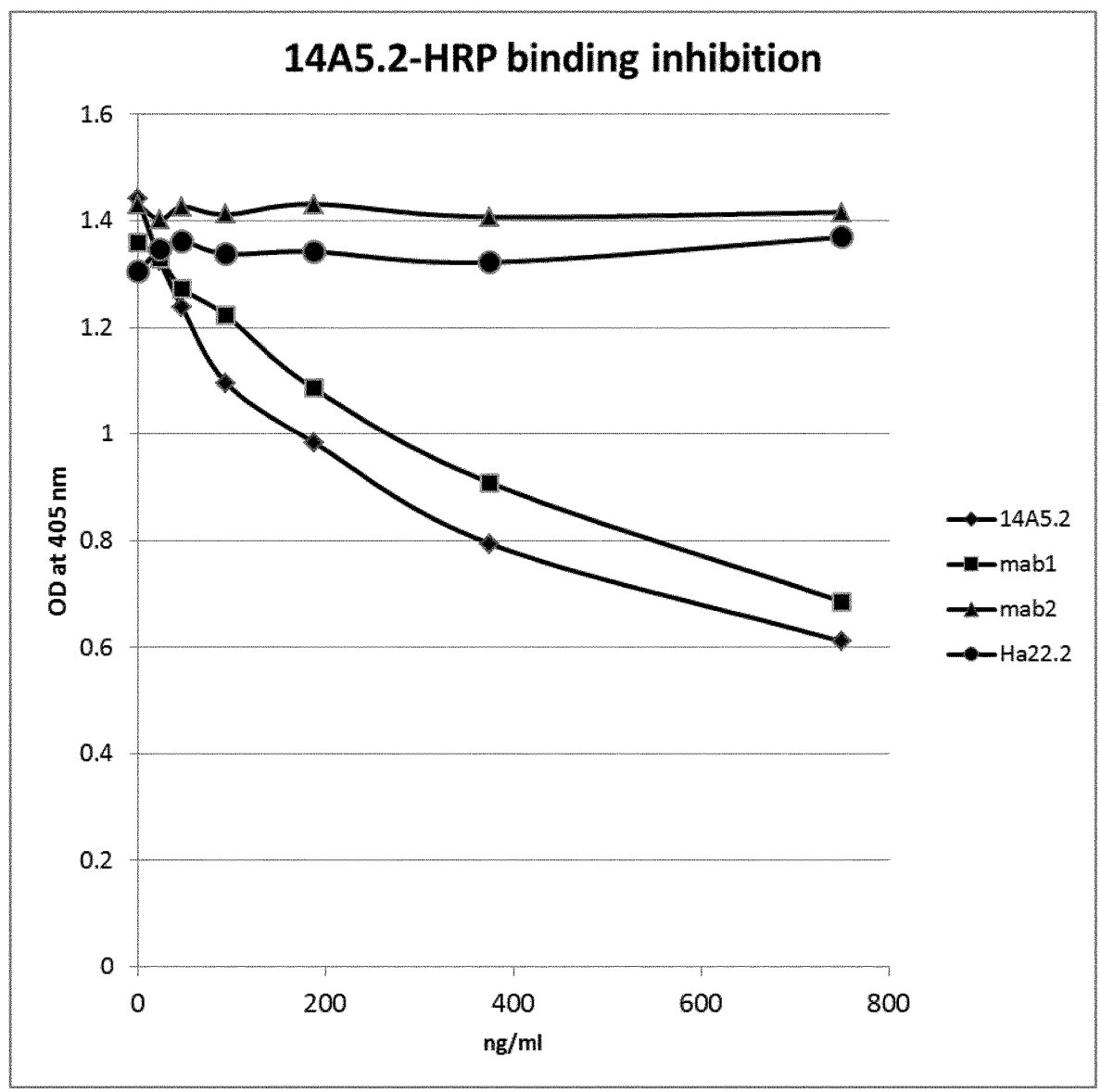

FIG. 2: Characterization of 14A5.2 epitope. Competition analysis was carried out by ELISA using different monoclonal antibodies as indicated. Binding of 14A5.2-HRP antibody to nectin-4 is inhibited by 14A5.2 itself and mab1, not by mab2 and Ha22-2.

Figure 3:
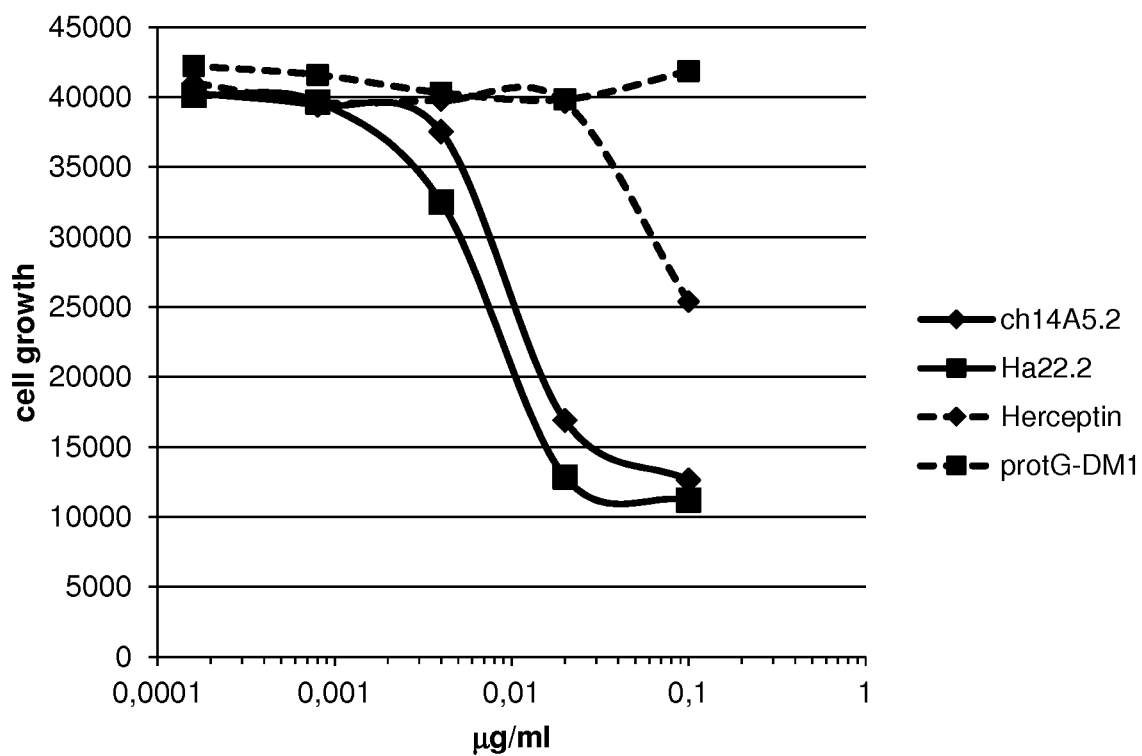

FIG. 3: Cytotoxicity induced by ch14A5.2 and Ha22-2 on SUM190 cells.

In this experiment, ADC is mimicked by incubation with indicated concentration of antibodies with protein-G-DM1. Cell growth was measured at day 5. 14A5.2 and Ha22.2 induced cytotoxicity with similar IC50. Efficiency is higher compared to Herceptin.

Figure 4:
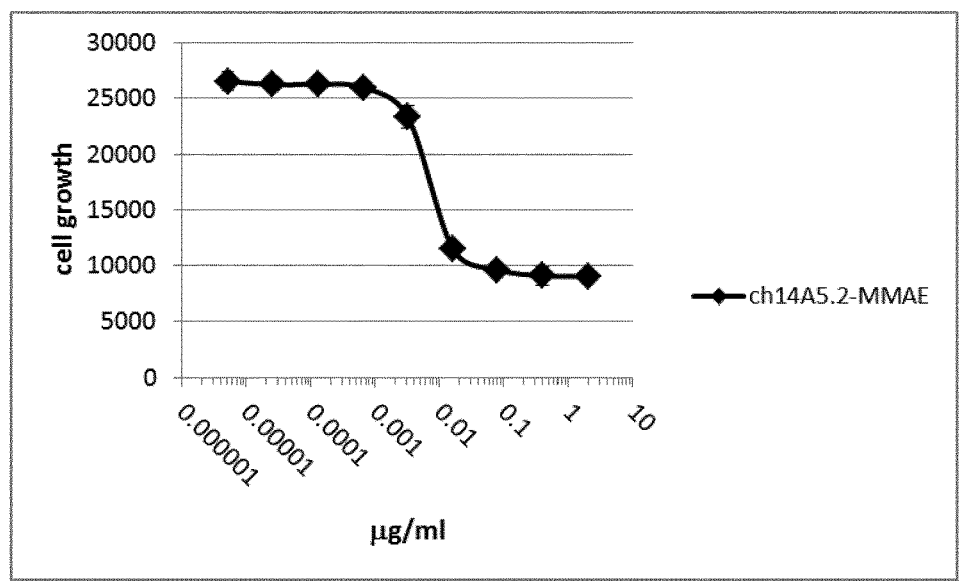
Figure 4:
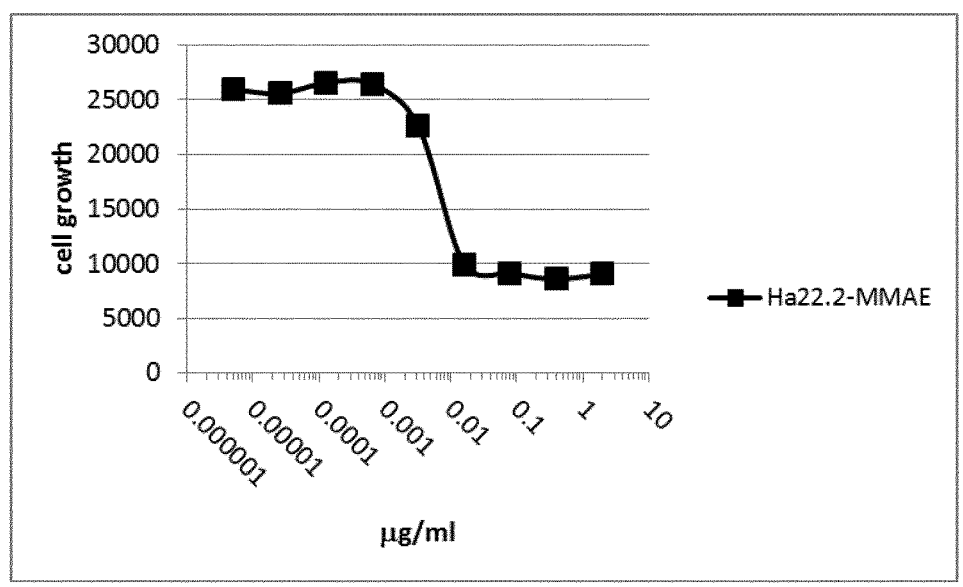

FIG. 4: Cytotoxicity induced by ch14A5.2-vc-MMAE and Ha22-2-vc-MMAE on SUM190 cells. IC50 was similar for both ADC (5 ng/ml).

Figure 5:
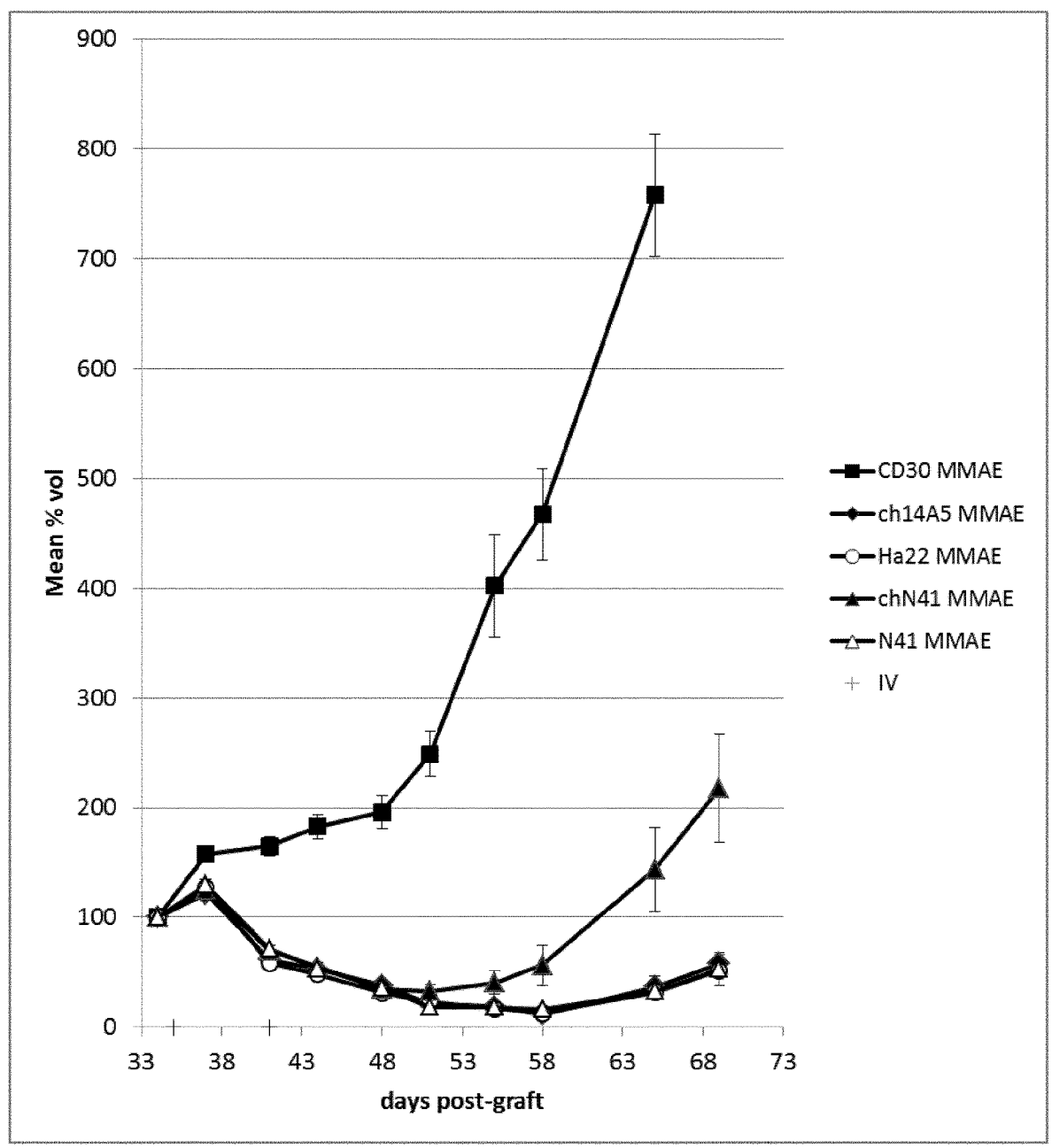

FIG. 5: Effect of chN41mab-vc-MMAE, N41mab-vc-MMAE, ch14A5.2-vc-MMAE and Ha22-2-vc-MMAE ADCs on tumor growth. SUM190 cells grown orthotopically as tumours in NSG mice show regression after a single treatment with the different ADCs (2 i.v. injections with 2.5 mg/kg (cross) at 6-days interval for all antibodies).

FIG. 6: A. ADCC induced by indicated concentration of antibodies. Luminescence corresponds to apoptosis of target cells. B. ADCC mediated lysis efficiency represents the maximum level of apoptosis for each antibody tested.

EXAMPLE

Material & Methods
Western-Blot

Nectin-4 expression was analysed in MDA-MB-231 wt or nectin-4 transfected cells in 100-mm dishes, washed 3 times with ice-cold PBS and then resuspended for 30 min in 750 μl of ice cold lysis buffer containing 50 mM Hepes, pH 7.5, 150 mM NaCl, 1.5 mM MgCl2, 1 mM EGTA, 1% Triton X-100, and 10% glycerol. A protease inhibitor mixture was added as recommended (Roche Diagnostics). Lysates were heated in SDS sample buffer (60 mM Tris-HCl, pH 6.7, 3% SDS, 2% (v/v) 2-mercaptoethanol, and 5% glycerol), separated by 8% SDS-PAGE, semidry-transferred to polyvinylidene difluoride membranes (Immobilon-P, Millipore, Boston, Mass., USA), probed with 1 μg/ml 14A5.2 monoclonal antibody. Visualization was done with ECL (Pierce).

Competition Assay

Mab competition assay was performed by ELISA. Ninety-six-well trays were coated with nectin4VCC-Fc overnight at +4° C. as indicated. Binding of peroxidase conjugated 14A5.2-HRP mab was measured in the presence of variable concentration of 4 different anti-nectin-4 mabs (mab1, mab2, mab3, and Ha22-2 mab).

Cytotoxicity Induced by ch14A5.2 and Ha22-2 (Also Known as ASG-22ME from Astellas Company) on SUM190 Cells To analyze the effect of humanized antibodies, SUM190 cells were incubated with indicated concentration of antibody in the presence of 0.65 nM protein-G-DM1. Cell growth was measured using the alamarBlue staining procedure as recommended by the manufacturer (Biosource, CA, USA). The test incorporates a fluorescent oxidation-reduction indicator. Fluorescence intensity is proportional to cellular metabolic reduction. Experiments were done by incubating 3000 cells/well at Day 0 in 96-well plates. AlamarBlue was measured at day 5 by incubating 1/10 volume of alamarBlue solution for 2 h at 37° C. and read at 595 nm (FLUOstar Optima, BMG Labtech).

Production of ADC

The ADC was produced by Concortis (San Diego, Calif., USA). Conjugates were produced from purified ch14A5.2 monoclonal antibody. The linker used was the MC-Val-Cit-PAB-PNP (Maleimidocaproyl-L-valine-L-citrulline-p-aminobenzyl alcohol p-nitrophenyl carbonate) covalently conjugated to monomethyl auristatin-E (MMAE). This cleavable linker was selected because it induced potent bystander killing. The drug-to-antibody ratio was approximately 4. To analyse the effect of ADC, SUM190 cells were incubated with indicated concentration of ADC. Cell growth was measured using the alamarBlue staining procedure as recommended by the manufacturer (Biosource, CA, USA). The test incorporates a fluorescent oxidation-reduction indicator. Fluorescence intensity is proportional to cellular metabolic reduction. Experiments were done by incubating 3000 cells/well at Day 0 in 96-well plates. AlamarBlue was measured at day 5 by incubating 1/10 volume of alamarBlue solution for 2 h at 37° C. and read at 595 nm (FLUOstar Optima, BMG Labtech).

Animal Models

All experiments were performed in agreement with the French Guidelines for animal handling and approved by local ethics committee (Agreement no 01152-01). NOD/SCID/γc null mice (NSG) were obtained from Dr. C. Rivers (Margate, UK). Mice were housed under sterile conditions with sterilized food and water provided ad libitum and maintained on a 12-h light and 12-h dark cycle. SUM190 cells were inoculated in the mammary fat pad with (0.5× 106) suspended in 50% phenol red-free Matrigel (Becton Dickinson Bioscience).

Tumor growth was monitored by measuring with a digital caliper and calculating tumor volume (length×width2×π/6). All animals were randomly assigned into treatment groups, such that the mean tumor volume for each group was 100 to 200 mm3. Treatment with ADC was performed as mentioned in the respective experiments.

Antibody-Dependent Cell-mediated Cytotoxicity (ADCC)

SUM190 target cells (10E5 cells) were plated on 96 wells white microplate overnight. NK cells were purified from healthy donors using the EasySep™ kit as recommended by the manufacturer. 10E6 cells (ratio E:T=10) were incubated with indicated concentrations of antibodies for 4 hours. Caspase-3/-7 activation was measured using the Caspase-Glo luminescent kit from Promega. Luminescence was measured after 30 min incubation (FLUOstar Optima, BMG Labtech).

Results

The 14A5.2 monoclonal antibody, presented herein, results from the selection of a series of anti-nectin-4 monoclonal antibodies according to stringent criteria, like specificity, epitope mapping, and anti-tumoral activity. This is of utmost important regarding the use in clinics, i.e, optimizing anti-tumoral activity with minimal adverse effects.

Western Blot

Among the series of anti-nectin-4 monoclonal antibodies, 14A5.2 detects an unique 72 kDa band in transfected cells not in cells transfected with null vector (FIG. 1). This m.w. corresponds to nectin-4 monomer as previously described (Reymond et al. JBC, 2001). MDAMB231 wt cells expressed nectin-1, nectin-2 and nectin-3. This indicates that 14A5.2 is highly specific for nectin-4 and does not detect other nectin members or other unrelated protein. Similar results were obtained by FACS analysis.

Competition Assay

Among the series of anti-nectin-4 monoclonal antibodies, we screened for antibodies that bind to an epitope different form Ha22-2. The 14A5.2 epitope is different for Ha22-2 in the IgV distal domain of nectin-4. As seen in FIG. 2, Ha22-2 did not compete for 14A5.2 binding. Mab1 is an anti-nectin-4 positive control (compete for 14A5.2 binding). Mab2 is an anti-nectin-4 negative control (did not compete for 14A5.2 binding).

Among the series of anti-nectin-4 monoclonal antibodies, we screened for monoclonal antibodies with strong binding affinity. Binding of the chimeric form of 14A5.2 was compared to Ha22-2 and showed similar affinity by FACS analysis (20 ng/ml) (data not shown).

Cytotoxicity Induced by ch14A5.2 and Ha22.2 on SUM190 Cells

This result (FIG. 3) indicates similar cytotoxic properties of ch14A5.2 (IC50=6 ng/ml) and Ha22.2 (IC50=5 ng/ml) in the presence of protein-G-DM1. In the same condition, we note that IC50 for trastuzumab is 100 ng/ml.

Production of ADC

This result (FIG. 4) indicates similar cytotoxic properties of ch14A5.2-MMAE and Ha22.2-MMAE. IC50 is 5 ng/ml.

In Vivo Experiments

Activity of our ADC was tested in immunocompromised NSG mice xenografted with the SUM190 cell line. Mice were treated with two successive i.v. doses of chN41-vc-MMAE, ch14A5.2-vc-MMAE and Ha22.2-vc-MMAE antibody (FIG. 5). CD30-vc-MMAE was used as an irrelevant control. These doses were not toxic for mice. Both ADCs induced a rapid (4 days) and marked tumour regression with a superior effect of ch14A5.2 compare to chN41, another anti-nectin-4 antibody of the inventor (the duration lasted up to 20 days).

More, the results in FIG. 5 showed that the chimeric 14A5.2 antibody (ch14A5.2-vc-MMAE) has the same efficacy than the fully murine antibody N41 (N41-vc-MMAE) which the Fc is functional in a mouse model (activation of immune system). Thus, even in the NGS (the mouse model used) phagocytosis or opsonization are still possible. We can conclude that if the 14A5.2 had a Fc functional in the mouse model (contrary to the ch14A5.2), this antibody would have a better efficacy than the N41 antibody.

Inhibition of Metastatic Progression from Primary Site In Vivo

Mice are orthotopically xenografted with luciferase-positive MDA-MB-231 cells expressing Nectin-4. The volume of primary tumors is measured after 35 days. Mice are treated i.v. with 10 mg/kg of naked 14A5.2 mab every week. Lungs and liver of killed mice are assayed by bioluminescence. Quantification is shown in for lungs and in for livers. Treatment of the orthotopically xenografted with two successive i.v. doses of 14A5.2 mab conjugated to MMAE induce a rapid reduction and disappearance of all metastatic lesions observed by luminescence analysis over 35 days (data not shown).

ADCC Assays

Figure 6A:
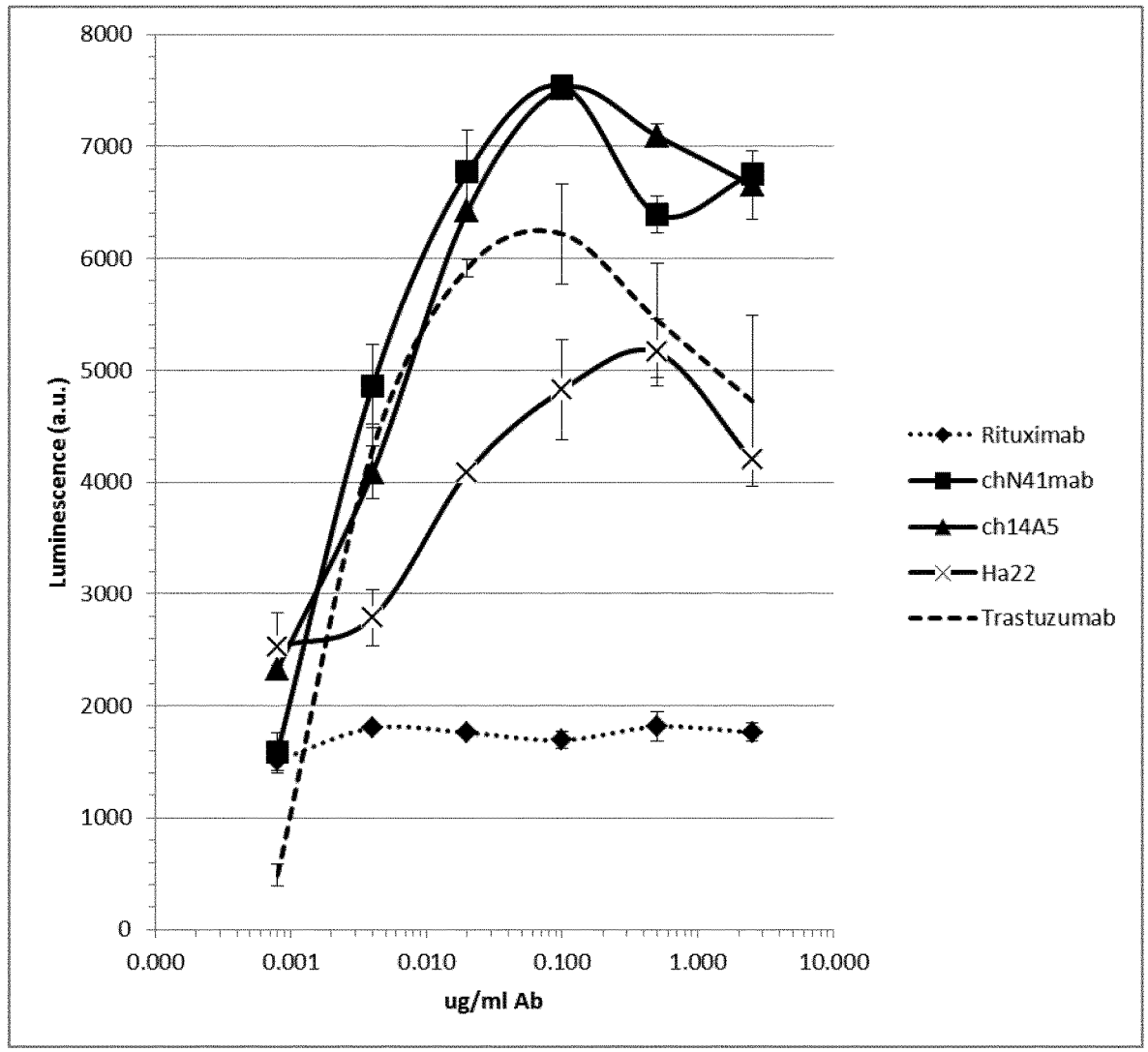
Figure 6B:
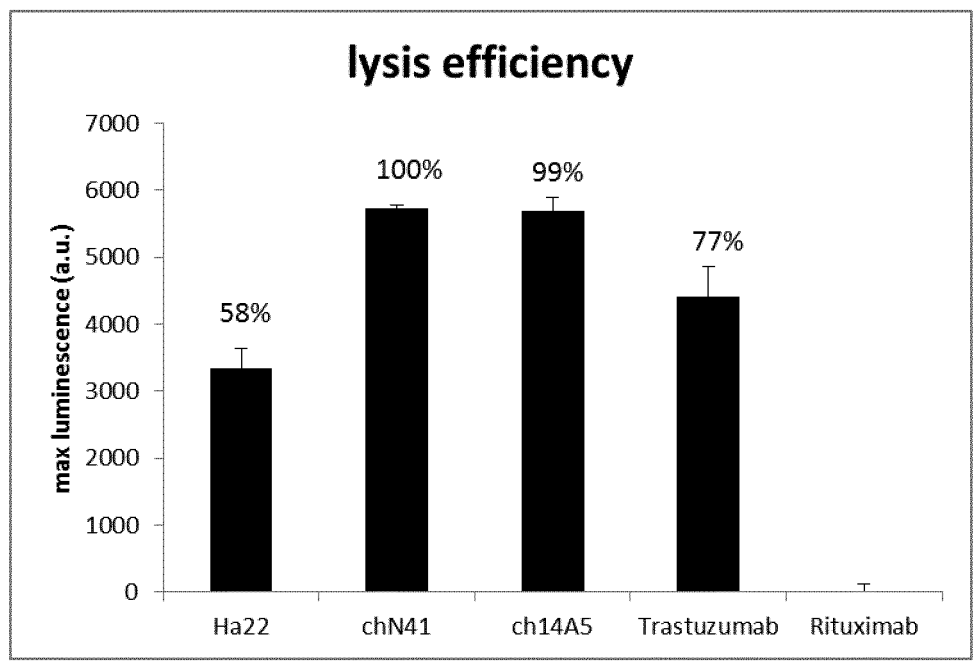

The ADCC activity of different antibodies including the 14A5.2 antibody were performed. The ADCC activity of the 14A5.2 was similar than the N41 antibody but 4 fold better than Ha22 in terms of IC50 (FIG. 6A). Lysis efficiency of 14A5.2 and N41 antibody was 2 fold better than Ha22 (FIG. 6B). Trastuzumab/Herceptin and Rituximab were used as positive and negative controls respectively.

Conclusions:

The different tests realized showed that the antibody 14A5.2 is better than N41 in ADC and is better than Ha22 in ADCC. 14A5.2 antibody is thus the best antibody tested (Table 1).

TABLE 1

Effects of the different antibodies tested

|  | ADC | ADCC |
|---|---|---|
| N41 | ++ | +++ |
| 14A5.2 | +++ | +++ |
| Ha22 | +++ | ++ |

REFERENCES

Throughout this application, various references describe the state of the art to which this invention pertains. The disclosures of these references are hereby incorporated by reference into the present disclosure.

The invention claimed is:

1. An antibody having a heavy chain comprising i) the H-CDR1 of 14A5.2 mab, ii) the H-CDR2 of 14A5.2 mab and iii) the H-CDR3 of 14A5.2 mab and a light chain comprising i) the L-CDR1 of 14A5.2 mab, ii) the L-CDR2 of 14A5.2 mab and iii) the L-CDR3 of 14A5.2 mab wherein the H-CDR1 of 14A5.2 mab is defined by the sequence ranging from the amino acid residue at position 31 to the amino acid residue at position 35 in SEQ ID NO:1;

the H-CDR2 of 14A5.2 mab is defined by the sequence ranging from the amino acid residue at position 50 to the amino acid residue at position 66 in SEQ ID NO:1;

the H-CDR3 of 14A5.2 mab is defined by the sequence ranging from the amino acid residue at position 99 to the amino acid residue at position 104 in SEQ ID NO:1;

the L-CDR1 of 14A5.2 mab is defined by the sequence ranging from the amino acid residue at position 24 to the amino acid residue at position 38 in SEQ ID NO:2;

the L-CDR2 of 14A5.2 mab is defined by the sequence ranging from the amino acid residue at position 54 to the amino acid residue at position 60 in SEQ ID NO:2 and the L-CDR3 of 14A5.2 mab is defined by the sequence ranging from the amino acid residue at position 93 to the amino acid residue at position 101 in SEQ ID NO:2.

2. An antibody according to claim 1 wherein the heavy chain has at least 70% of identity with SEQ ID NO:1 and the light chain has at least 70% of identity with SEQ ID NO:2.

3. An antibody according to claim 2 wherein the heavy chain is identical to SEQ ID NO:1 and the light chain is identical to SEQ ID NO:2.

4. The antibody of claim 1 wherein the antibody is a chimeric antibody.

5. The antibody of claim 1 wherein the antibody is a humanized antibody which comprises the CDRs of the 14A5.2 mab antibody.

6. A nucleic acid molecule encoding the antibody of claim 1.

7. The antibody of claim 1 wherein the antibody is conjugated to a cytotoxic moiety.

8. The antibody of claim 7 wherein the cytotoxic moiety is selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor; an antimitotic agent; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite; an alkylating agent; a platinum derivative; duocarmycin A, duocarmycin SA, rachelmycin (CC-1065), or an analog or derivative thereof; an antibiotic; pyrrolo[2,1-c][1,4] benzodiazepine (PDB); a toxin; ribonuclease (RNase); DNase I; and pokeweed antiviral protein.

9. A pharmaceutical composition comprising the antibody of claim 1.

10. The antibody of claim 8, wherein the tubulin-inhibitor is maytansine or an analog or derivative thereof;

the antimitotic agent is monomethyl auristatin E or F or an analog or derivative thereof;

the antimetabolite is methotrexate, 6 mercaptopurine, 6 thioguanine, cytarabine, fludarabin, 5 fluorouracil, decarbazine, hydroxyurea, asparaginase, gemcitabine, or cladribine;

the alkylating agent is mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine or mitomycin C;

the platinum derivative is cisplatin or carboplatin;

the antibiotic is dactinomycin, bleomycin, daunorubicin, doxorubicin, idarubicin, mithramycin, mitomycin, mitoxantrone, plicamycin or anthramycin (AMC);

the toxin is a diphtheria toxin, a ricin toxin, a cholera toxin, a Shiga-like toxin, LT toxin, C3 toxin, Shiga toxin, pertussis toxin, tetanus toxin, soybean Bowman-Birk protease inhibitor, *Pseudomonas* exotoxin, *Pseudomonas* endotoxin, alorin, saporin, modeccin, gelanin, abrin A chain, modeccin A chain, alpha-sarcin, an *Aleurites fordii* protein, a dianthin protein, a *Phytolacca americana* protein, *Momordica charantia* inhibitor, curcin, crotin, *Sapaonaria officinalis* inhibitor, gelonin, mitogellin, restrictocin, phenomycin, neomycin or Staphylococcal enterotoxin A.

* * * * *

SEQUENCE LISTING

<160> NUMBER OF SEQ ID NOS: 2

<210> SEQ ID NO 1
<211> LENGTH: 115
<212> TYPE: PRT
<213> ORGANISM: Mus musculus

<400> SEQUENCE: 1

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Thr Met Asp Trp Val Lys Gln Ser His Gly Lys Ser Leu Glu Trp Ile
        35                  40                  45

Gly Asp Ile Asn Pro Asn Asn Asp Val Thr Met Tyr Asn Glu Lys Phe
    50                  55                  60

Lys Gly Arg Ala Thr Leu Thr Val Asp Lys Ser Ser Ser Thr Ala Tyr
65                  70                  75                  80

Met Glu Val Arg Ser Leu Thr Ser Glu Asp Thr Ala Val Tyr Tyr Cys
                85                  90                  95

Val Arg Gly Arg Gly Phe Ala Tyr Trp Gly Gln Gly Thr Leu Val Thr
            100                 105                 110

Val Ser Ala
        115

<210> SEQ ID NO 2
<211> LENGTH: 111
<212> TYPE: PRT
<213> ORGANISM: Mus musculus

<400> SEQUENCE: 2

Asp Ile Val Leu Thr Gln Ser Pro Ala Ser Leu Ile Val Ser Leu Gly
1               5                   10                  15

Gln Arg Ala Thr Ile Ser Cys Arg Ala Ser Gln Ser Val Ser Thr Ser
            20                  25                  30

Ser Asn Ser Tyr Met His Trp Tyr Gln Gln Lys Pro Gly Gln Pro Pro
        35                  40                  45

Lys Leu Leu Ile Arg Phe Ala Ser Asn Leu Glu Ser Gly Val Pro Ala
    50                  55                  60

Arg Phe Ser Gly Ser Gly Ser Gly Thr Tyr Phe Thr Leu Asn Ile His
65                  70                  75                  80

Pro Val Glu Glu Glu Asp Ser Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110